(12) United States Patent
Miethke

(10) Patent No.: US 12,005,215 B2
(45) Date of Patent: Jun. 11, 2024

(54) FLOW REDUCER

(71) Applicant: Christoph Miethke GmbH & Co KG, Potsdam (DE)

(72) Inventor: Christoph Miethke, Potsdam (DE)

(73) Assignee: Christoph Miethke GmbH & Co KG, Potsdam (DE)

( * ) Notice: Subject to any disclaimer, the term of this patent is extended or adjusted under 35 U.S.C. 154(b) by 755 days.

(21) Appl. No.: 16/500,056

(22) PCT Filed: Mar. 29, 2018

(86) PCT No.: PCT/EP2018/000135
§ 371 (c)(1),
(2) Date: Oct. 1, 2019

(87) PCT Pub. No.: WO2018/184717
PCT Pub. Date: Oct. 11, 2018

(65) Prior Publication Data
US 2021/0100989 A1     Apr. 8, 2021

(30) Foreign Application Priority Data

Apr. 6, 2017    (DE) ...................... 10 2017 003 366.8
Jul. 28, 2017    (DE) ...................... 10 2017 007 093.8
(Continued)

(51) Int. Cl.
*A61M 27/00*     (2006.01)

(52) U.S. Cl.
CPC ................. *A61M 27/006* (2013.01)

(58) Field of Classification Search
CPC .. A61M 27/00; A61M 27/002; A61M 27/006; A61M 2202/0464; A61M 1/70
See application file for complete search history.

(56) References Cited

U.S. PATENT DOCUMENTS 3,566,875 A    3/1971   Stoehr
3,889,687 A    6/1975   Harris et al.
(Continued)

FOREIGN PATENT DOCUMENTS

CN     105769199 A    7/2016
DE     3835788 A1    4/1990
(Continued)

OTHER PUBLICATIONS

Alfred Aschoff, "In-Vitro-Testung von Hydrozephalus Ventilen", p. 32, 1994.
(Continued)

*Primary Examiner* — Philip R Wiest
(74) *Attorney, Agent, or Firm* — Smartpat PLC

(57) ABSTRACT

The application relates to a hydrocephalus valve for draining CSF from the ventricle systems of patients. The valve has a housing with a housing interior and at least one first passage for admission and/or discharge. The valve has at least one body provided in the housing interior. The body is designed to move in at least one direction. At least one adjusting unit is provided. The application aims to improve tried-and-tested existing valves. To achieve this, the adjusting unit is designed to adjust at least one drainage rate in the passage, and to allow the drainage rate to be adjusted between 1 ml per hour and 1000 ml per hour at a pressure at the hydrocephalus valve of 20 cm water column, in order to slow or accelerate, by means of this adjustment, a change in pressure in the ventricle system that results from the drainage.

28 Claims, 15 Drawing Sheets

(30) Foreign Application Priority Data

Feb. 6, 2018 (DE) ...................... 10 2018 000 941.7
Feb. 21, 2018 (DE) ...................... 10 2018 001 392.9

(56) References Cited

U.S. PATENT DOCUMENTS

| | | |
|---|---|---|
| 4,676,772 A | 6/1987 | Hooven |
| 5,037,062 A | 8/1991 | Neuhaus |
| 5,167,615 A | 12/1992 | East et al. |
| 5,928,182 A | 7/1999 | Kraus et al. |
| 6,077,219 A | 6/2000 | Viebach et al. |
| 8,870,809 B2 | 10/2014 | Miethke |
| 2003/0139699 A1 | 7/2003 | Rosenberg |
| 2004/0024346 A1 | 2/2004 | Miethke |
| 2005/0178988 A1 | 8/2005 | Biehl et al. |
| 2011/0275976 A1 | 11/2011 | Negre et al. |
| 2012/0046595 A1 | 2/2012 | Wilson et al. |
| 2012/0226215 A1 | 9/2012 | Hsu et al. |
| 2012/0302938 A1 | 11/2012 | Browd et al. |
| 2012/0316492 A1 | 12/2012 | Chappel |
| 2013/0085441 A1* | 4/2013 | Aihara .............. A61M 5/14276 604/9 |
| 2014/0005588 A1 | 1/2014 | Miethke |
| 2014/0276339 A1* | 9/2014 | Wilson .................... F16K 31/08 604/9 |
| 2014/0276348 A1 | 9/2014 | Alan |
| 2014/0336560 A1 | 11/2014 | Hakim |
| 2015/0182734 A1* | 7/2015 | Miethke .............. A61M 27/006 604/9 |
| 2017/0354337 A1 | 12/2017 | Schmidt et al. |
| 2018/0126147 A1* | 5/2018 | Hakim ................. A61B 5/4836 |
| 2018/0184943 A1* | 7/2018 | Boden, Jr. ........... A61M 27/006 |
| 2019/0060621 A1* | 2/2019 | Bertrand ............. A61M 27/006 |
| 2019/0344058 A1 | 11/2019 | Hakim |

FOREIGN PATENT DOCUMENTS

| | | |
|---|---|---|
| DE | 69808558 T2 | 6/2003 |
| DE | 10258071 A1 | 6/2004 |
| DE | 102007059300 A1 | 6/2009 |
| EP | 1343557 | 9/2003 |
| EP | 0873761 B1 | 11/2004 |
| EP | 1523635 A1 | 4/2005 |
| EP | 1331019 B1 | 3/2006 |
| EP | 2359886 A1 | 8/2011 |
| EP | 2777751 A2 | 9/2014 |
| JP | 850124488 A | 9/1975 |
| JP | 2006020905 A | 1/2006 |
| JP | 2011513024 A | 4/2011 |
| JP | 2011229601 A | 11/2011 |
| JP | 2012040388 A | 3/2012 |
| JP | 2015531255 A | 11/2015 |
| WO | 9117779 A1 | 11/1991 |
| WO | 2012065750 A2 | 5/2012 |
| WO | 2014144703 A2 | 9/2014 |

OTHER PUBLICATIONS

DIN Deutsches Institut für Normung e.V., Neurochirurgische Implantate—Sterile Hydrozephalus-Shunts zum Einmalgebrauch und deren Bestandteile (ISO 7197:2006, einschließlich Cor 1:2007); Deutsche Fassung EN ISO 7197:2009; Aug. 2009.

DIN Deutsches Institut für Normung e.V., Nichtaktive chirurgische Implantate—Allgemeine Anforderungen (ISO 14630:2008); Deutsche Fassung EN ISO 14630:2009; Aug. 2009.

Fritsch, Michael J., et al., Normal pressure hydrocephalus: pathophysiology, diagnosis, treatment. Stuttgart New York: Thieme, 2014.

Kombogiorgas, Dimitris, The cerebrospinal fluid shunts. pp. 130/131. New York: Nova Science Publishers, Inc, 2016.

Sainte-Rose; Hooven; Hirsch, "A new approach in the treatment of hydrocephalus", Neurosrg, (19870000), vol. 66, No. 2, pp. 213-226.

* cited by examiner

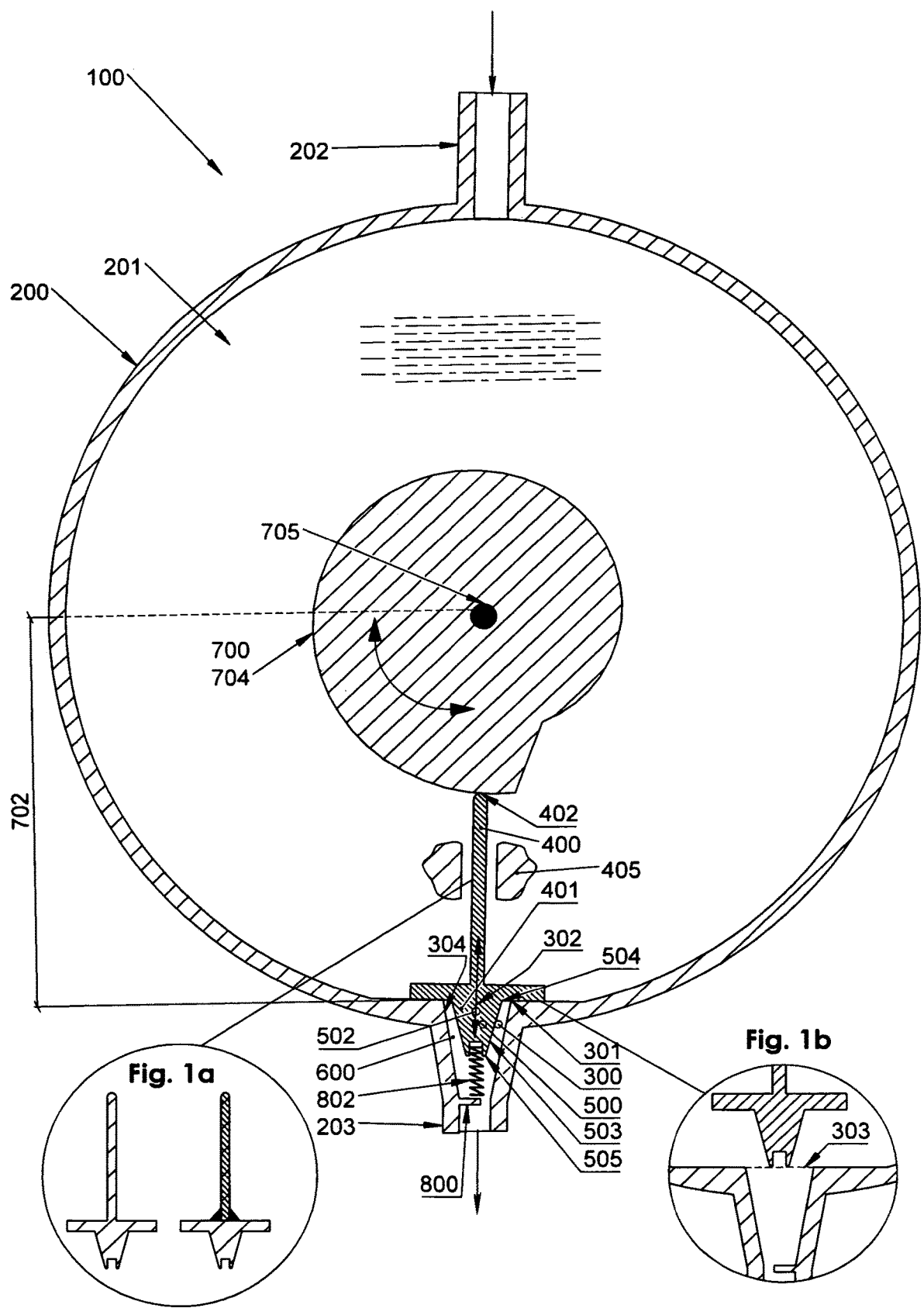

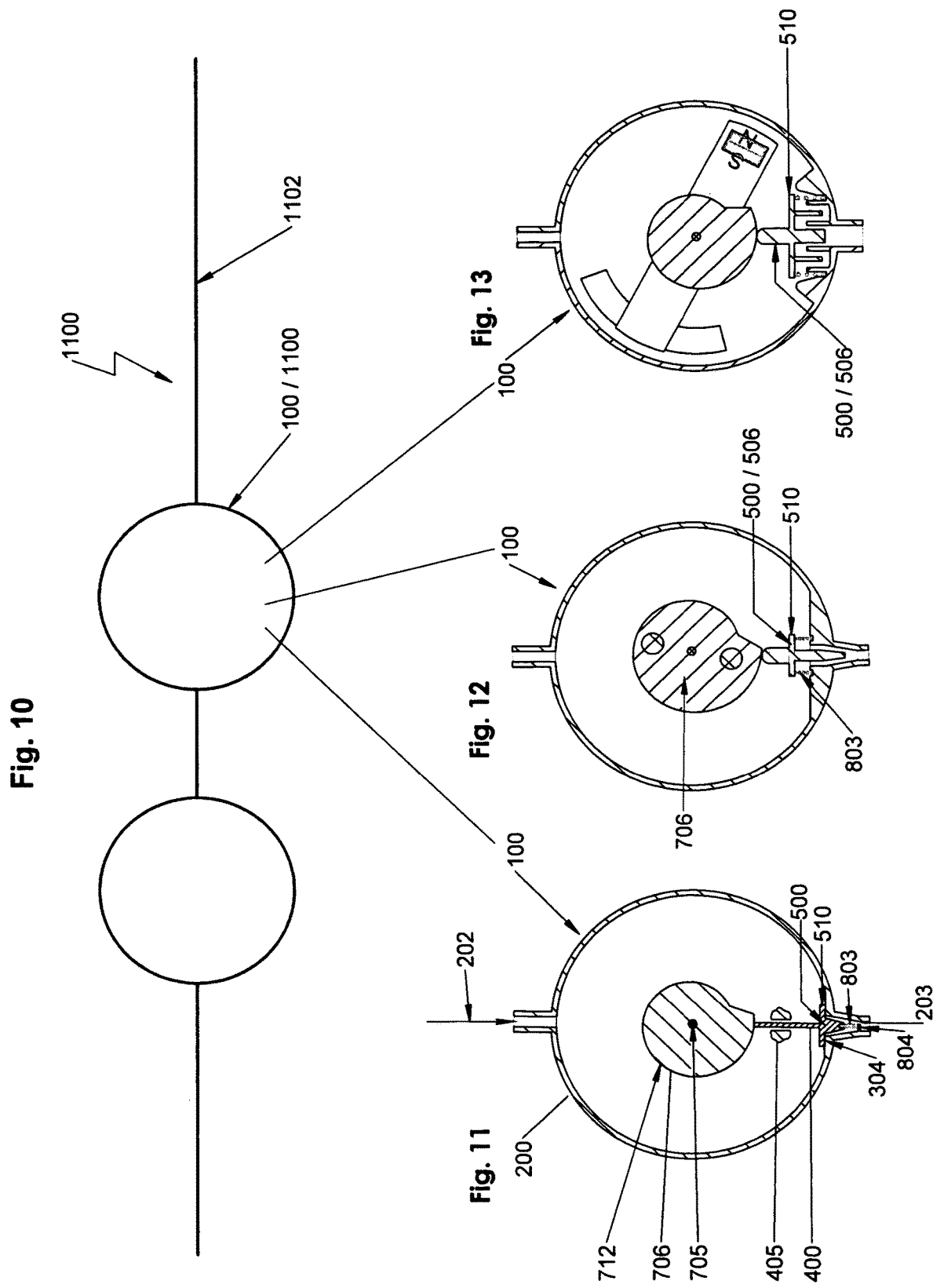

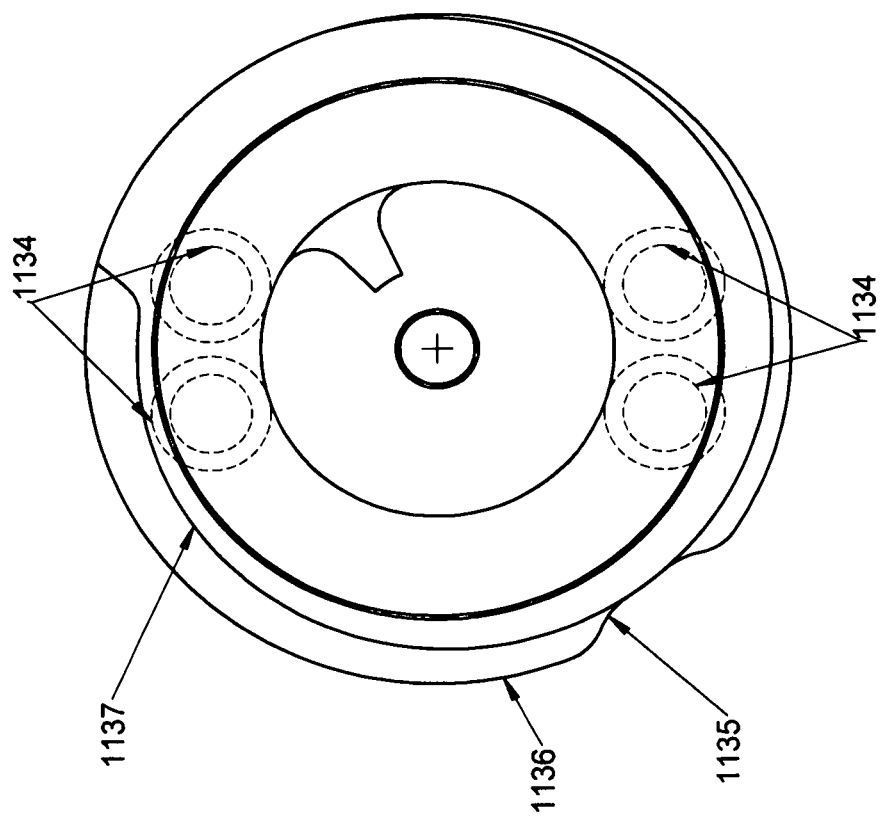

FLOW REDUCER

TECHNICAL FIELD

The invention relates to a hydrocephalus valve for draining fluid from ventricular systems of patients, which valve has at least one casing with casing interior, at least one first passage for admission and/or discharging, with at least one body which is arranged in the casing interior, wherein the body is designed to be movable at least in one direction and which valve has at least one adjusting unit.

BACKGROUND

Hydrocephalus patients have the following medical problem:

The brain is surrounded, in the cranium, by cerebrospinal fluid (CSF). CSF is constantly produced and resorbed in equal quantities. In the case of disease of the hydrocephalus, also referred to as water on the brain, this equilibrium is disrupted. Since the cranium constitutes a closed vessel, an enlargement occurs if more CSF is produced than is resorbed. Owing to the enlargement, in infants, the cranial sutures cannot fuse, and in adults, the cranial internal pressure increases. Adult hydrocephalus and pediatric hydrocephalus therefore exist.

Hydrocephalus can be distinguished in terms of its forms into hydrocephalus internus, hydrocephalus externus, hydrocephalus internus et externus, normal pressure hydrocephalus and hydrocephalus e vacuo.

The treatment of hydrocephalus was originally performed by simply draining the CSF. This was done simply by way of a hose connection between the cranium and a large venous blood vessel or by way of a corresponding connection of the cranium via a hose to the abdominal cavity. It was however soon identified that the pressure in the cranium must have a particular physiological value if other complications are not to arise.

Modern hydrocephalus therapies utilize an implantable drainage facility, an artificial connection between the cerebral ventricles in the head and a drainage compartment, nowadays normally the abdominal cavity, in order to set a particular physiological value.

Various drainage facilities are known with which the pressure in the cranium of a patient can be treated. The drainage facilities are intended to open at a particular critical pressure and allow the drainage of fluid—also referred to as cerebrospinal fluid—such that the generation of an overpressure in the cranium is prevented. These drainage facilities for protecting against an overpressure of cerebrospinal fluid (CSF) are commonly referred to as so-called shunts or drains.

The core of the implantable drainage facility is an implantable valve by way of which the drainage facility is controlled. Said valve is referred to as hydrocephalus valve. Hydrocephalus valves are generally implanted closely under the skin. Such drainage facilities are generally implanted under the skin in the region of the head.

One possible definition of the expression "shunt" is given by Miethke: any artificial hydraulic connection between a first body part which contains cerebrospinal fluid and a second body part which can receive same, see The Cerebrospinal Fluid Shunts, pages 130/131 (source 1). On the topic of hydrocephalus, further sources are the book Normal Pressure Hydrocephalus, Fritsch et al., 2014 (source 2) and the standards EN ISO 7197 (source 3) and EN ISO 1463 (source 5).

All sources contain, inter alia, technical expressions and definitions relating to the topic hydrocephalus. They also contain known operating principles and the grouping thereof.

Miethke proposes, in source 1, a twofold grouping, in this regard see table 1. In a first sub-grouping, the differentiates valves, in accordance with their operating principles, into differential pressure valves and hydrostatic valves. In a second sub-grouping, the differentiates valves, in accordance with clinical functions, into fixed, that is to say non-adjustable, and adjustable valve types.

TABLE 1

| operating principles of shunts, source 1, page 117 | | |
|---|---|---|
| Valve | Fixed | Adjustable |
| Differential pressure valves | | |
| Silicone slit valves | X | |
| Membrane valves | X | |
| Ball cone valves | X | X |
| Hydrostatic valve principles | | |
| Anti-siphon device principles | X | |
| Flow-reducing principles | X | |
| Gravitation-based principles | X | X |

The valves of the group of the hydrostatic valve principle are, according to Miethke, referred to as valves or valve components, the design objective of which is based on preventing excessive drainage (source 1, page 67). The objective of the valves of this group is in this case to compensate a force of a hydrostatic pressure that acts in the direction of a valve opening (so-called counterbalance).

Valves with a hydrostatic operating principle can be differentiated into three valve types. These are referred to as anti-siphon, flow-controlled and gravitation-controlled devices. Common to all three valve types is a differential pressure. This is calculated from the difference between the pressure downstream of the valve minus the pressure upstream of the valve ($\Delta p = p_{downstream\ of\ the\ valve} - p_{upstream\ of\ the\ valve}$). The pressure difference that permits a volume flow through the valve is defined as opening pressure of the valve.

Anti-siphon devices adapt their opening pressure to the magnitude of a suction force acting in the valve. Gravitation-controlled devices adapt the opening pressure to their inclination in the Earth's gravitational field. By contrast, flow-controlled devices adapt the volume flow passing through them to the pressure difference.

Similar terms for volume-flow-adapting valves in the prior art are flow-rate-dependent, flow-regulating or flow-reducing valves or devices. Here, the term flow is generally to be considered equivalent to the term volume flow, volume per unit of time.

Any hydrocephalus valve is characterized by a characteristic curve. Dr. med. Alfred Aschoff describes characteristic curves in In-Vitro-Testung von Hydrozephalus Ventilen [In vitro testing of hydrocephalus valves], 1994, page 32 (source 7). He discusses these therein because shunt valves are flow controllers with unidirectional direction preference. According to Aschoff, said shunt valves are distinguished by the fact that they are characterized firstly by a unidirectional action, secondly by an opening and closing characteristic, and thirdly by a specific pressure-flow characteristic curve. The pressure-flow characteristic curve is normally non-linear. The profile thereof is, according to Aschoff, dependent on the hydrocephalus valve itself, such that a hydrocephalus valve can be described only by specifying the complete characteristic curve.

Non-adjustable hydrocephalus valves are characterized by one valve characteristic curve, whereas adjustable hydrocephalus valves are characterized by multiple valve characteristic curves.

In the case of non-adjustable hydrocephalus valves, it is evident that valves of the group of the hydrostatic valve principle exhibit a particular volume flow, a throughflow, in a manner dependent on the fluid pressure. If an associated volume flow for every fluid pressure is plotted on a graph, this yields a valve characteristic curve.

In the case of adjustable hydrocephalus valves, every adjustment configures the valve. Every configuration yields a different valve characteristic curve. Certain relevant hydrocephalus valves are described below.

U.S. Pat. No. 8,870,809 B2 (Christoph Miethke GmbH & Co KG) relates to an implantable hydrocephalus system for the treatment of hydrocephalus patients with medications. The document presents an implantable hydrocephalus system with which it is also possible for medications to be administered into the patient. For this purpose, the medications must be introduced into a hollow space, a cavity of the hydrocephalus system, such that they can be transferred hydraulically from there through a ventricular catheter into the cerebral ventricle. According to the teaching, for this purpose, a system is necessary that, in one state, receives medicinal fluids and, in another state, transfers these in the direction of the cerebral ventricle. The system thus necessitates a valve and therefore comprises a valve arrangement with a valve flap in a casing with an inlet and an outlet. The valve arrangement in the valve opens or closes the inlet of the hydrocephalus system in a manner dependent on the medicinal fluid pressure in the cavity.

The teaching of DE 38 35 788 A1 concerns, as per EP 1 523 635 B1 paragraph [0003] (Aesculap AG), a fast-switching ball valve. In one state, medicinal fluid is received, and in another state, said medicinal fluid is released in the direction of the brain. In the closed state of the valve, the ball is pressed against the passage opening. To open up the passage opening, the actuating mechanism pushes the ball laterally away from the passage opening. For this purpose, an actuating element of the actuating mechanism exerts a lateral pushing action on the ball, which thereupon moves away from the passage opening or the valve seat of the passage opening. As an actuating mechanism for displacing the ball, use is made here of a pulse-driven electromagnet, which, after an actuation, is pulled back into the initial position again by a spring force.

EP 1 523 635 B1 (Aesculap AG) offers a solution for providing a valve that permits actuating travels in the millimeter range. In principle, the proposal combines a main body with a passage opening and two elements in wire form, in particular SMA (shape memory alloy) wires. These reciprocally shorten in a manner dependent on a temperature change. In a particularly advantageous embodiment, the result is a valve with a binary opening characteristic. Phenomenologically, a function of a switch results from a position manipulation of a body upstream of a passage opening.

US 2015 0182 734 A1 (Christoph Miethke GmbH & Co KG) discloses an adjustable hydrocephalus valve, programmable gravitation assistant, for pressure adjustment in the cranium of a hydrocephalus patient. For this purpose, by way of a membrane, a brake is released in order to release a rotor such that the latter can be rotated freely about an axis. By way of an acoustic signal, a click, the membrane signals the release or blockage of the rotor to a user. Because magnets are installed therein, the rotor is rotatable about its axis by way of a likewise magnetic tool. The rotation is utilized to adjust a valve characteristic. The valve has proven successful.

U.S. Pat. No. 4,676,772 (Cordis Cooperation) disclosed, as early as 1985, a system for pressure control of cerebrospinal fluid. Said system comprises an implantable pressure relief valve for fluids, which pressure relief valve has a casing and an adjusting unit in order to adjust the opening pressure of the pressure relief valve. Here, in a manner dependent on a pressure prevailing at the pressure relief valve, a membrane is deflected such that a passage between a sealing ring embedded in the membrane and a ball is opened. The ball is, for this purpose, mounted in a pot, into the lateral surface of which a thread is cut. By way of the thread, the pot can be screwed into or out of a cover, such that a pressure between the ball and the sealing ring is adjustable. The position of the pot, that is to say the number of screwed-in thread turns in the pressure relief valve, can be depicted via a magnetic bridge on a display device.

In summary, the teaching of U.S. Pat. No. 4,676,772 concerns a setting of a valve opening pressure, but disadvantageously not the setting of a defined volume flow. Furthermore, the described technology has the disadvantage that a setting of a valve opening pressure by virtue of a pot being screwed in can lead to a plastic deformation of the membrane. This arises if, as a result of the pot being screwed in too far, the membrane is subjected, via the ball, to a force which exceeds the elasticity limit of the membrane. A precise setting of a valve opening pressure necessitates a precise positioning of the pot in the cover. The pot is rotated in the cover via a magnetic bridge, which corresponds to a hand movement of a user. The user however is not provided with any feedback regarding the friction or the relative position between pot and cover. Thus, because the pot in the cover is turned too far or not far enough by the user, said pot is not positioned precisely, such that the valve opening pressure cannot be precisely set.

The so-called Orbis Sigma valve was proposed by Sainte-Rose, Hooven and Hirsch in: A new approach in the treatment of hydrocephalus, Neurosrg, 1987, 66(2), 213-26. The Orbis Sigma valve comprises a sapphire membrane with a bore, and a pin which extends through said bore. Here, the pin has, in its cross section, an undercut in the direction of its end facing toward the membrane. The membrane is mounted along its circumference in a casing in a flow channel. The pin is mounted at its end averted from the membrane in the same casing and the same flow channel. If a differential pressure prevails across the membrane, said membrane deflects by bulging with the pressure gradient. The degree of bulging and the form of the undercut in the pin thus then define a passage. The size of said passage varies with the profile of the undercut. Thus, the Orbis Sigma valve adjusts the size of a passage continuously along a differential pressure prevailing across a membrane in interaction with a profile of an undercut.

The disadvantage of the Orbis Sigma valve is the dependency thereof on the differential pressure. Furthermore, the profile of the undercut cannot be assumed to be constant for all patients. It must rather be adapted to the respective severity of the hydrocephalus of a patient.

EP 0873761 B1 (DePuy) describes a device for limiting a liquid flow. The device exhibits the principle of a so-called SiphonGuard®. Said document disclosed, in 1998, a technology for limiting a flow of a fluid from a first region of a patient to a second region. For this purpose, the device comprises an inlet, for admitting the fluid from a first region, and an outlet, for conducting the fluid into a second region. Furthermore, the device comprises a primary flow path and a secondary flow path, which both fluidically communicate with the inlet and the outlet. A detector in the device can detect the flow rate, the volume flow of the fluid, such that, in a manner dependent on the magnitude thereof, a decision can be taken as regards whether said fluid is conducted along the primary or the secondary flow path. Here, the detector makes the decision by comparing a present flow rate with a threshold value. The detector conducts the fluid from the inlet to the outlet along the primary flow path if the fluid flow rate is lower than a predefined threshold value. Conversely, the detector conducts the fluid from the inlet to the outlet along the secondary flow path if the flow rate is higher than a predefined threshold value. Here, the detector is made up of four components, a ball seat, a ball, a leaf spring and a spiral spring. The leaf spring presses the ball out of the ball seat, whereas the spiral spring presses the ball into the ball seat. The difference between the two spring strengths thus defines the threshold value of the detector.

The device for limiting a fluid flow thus adjusts its flow resistance digitally between two states, high flow resistance and low flow resistance. It thus has the disadvantage of subjecting the magnitude of a flow resistance to adjustability between two states, without keeping the magnitude of a volume flow constant. Both the size of the passage of the primary flow path and the size of the passage of the secondary flow are predefined at the factory by the design of the device.

US 2014/0276348A1 (DePuy-Synthes Products, Inc.) from the year 2013 discloses an overvoltage protection unit which is based on the principle of the so-called "Siphon-Guard®". Said overvoltage protection unit comprises a casing with an inlet and an outlet and with a first flow path within the casing. The first flow path connects the inlet to the outlet. Additionally, the casing comprises a second flow path, which likewise connects the inlet and the outlet. Both flow paths have a respective flow resistance. The flow resistance of the second flow path is relatively greater than the flow resistance of the first flow path. Within the first flow path, there is provided a valve with a valve seat and a first valve ball and a second valve ball. The first valve ball is positioned so as to be movable between a closure position, in which the first valve ball is in contact with the valve seat, and an opening position, in which the first valve ball is spaced apart from the valve seat. Here, the first valve ball is arranged between a second valve ball and the valve seat, and the second valve ball is arranged so as to be movable between a closure position and an opening position.

The valve opening pressure, the weight force of both balls in relation to the contact area of the first ball in the valve seat, is advantageously adapted by way of the position of both balls in the Earth's gravitational field. The greater the angle between a vertical and the vertical axis of the valve, the lower the weight force of both balls is in relation to the contact area of the first ball in the valve seat. Thus, the valve opening pressure decreases as the patient with the valve moves from a vertical position into a horizontal position.

The association of the valve opening pressure exclusively with the valve orientation in the Earth's gravitational field is disadvantageous.

Also, the overvoltage protection unit has a disadvantage: the flow resistance of the second flow path is predefined at the factory by the construction thereof. The parameters of the flow resistance, such as for example the number of thread turns and the thread pitch thereof, cannot be adjusted after implantation.

EP 13310192 also discloses a flow-controlled device (Codman). This apparatus, referred to in the publication document itself as anti siphon shunt, discloses, in accordance with the differentiation according to Miethke, a self-adjusting flow-controlled valve, but not an adjustable valve. The anti siphon shunt for regulating a volume flow in a patient comprises a casing, which defines a fluid chamber, and an inlet opening and an outlet opening. The inlet opening serves for a passage of a fluid into the fluid chamber, and the outlet opening serves for the release of said fluid. Additionally, the anti siphon shunt comprises a valve mechanism for regulating the fluid flow through the fluid chamber on the basis of the pressure gradient prevailing across said fluid chamber. For this purpose, the valve mechanism has, in the fluid chamber, a barrier which exhibits an opening through which fluid can pass. Furthermore, the anti siphon shunt comprises a pressure sensor for detecting the external pressure surrounding the fluid chamber, and a preloading element, for example a spring. The latter is operatively connected to the pressure sensor and serves for imparting a first force against a first surface of a ball. As a result, the ball is pressed against the opening, such that a passage of the fluid through the barrier and consequently through the fluid chamber is prevented. A compensating force acts on a second surface of the ball in a direction opposite to the first force. Both the first and the second surface are in this case of approximately equal size.

The ball is intended to close the opening in the barrier by way of a ball until an opening pressure is attained which exceeds the ratio of the difference between the first force minus the compensating force.

In a further embodiment, the document discloses a second technical facility for displacing one end of the preloading element, the spring, such that the preload force thereof changes. For this purpose, the document proposes connecting the peritoneal cavity to the fluid chamber by way of a first channel. The latter may for example be a hose. The proposal furthermore includes a reference chamber, which is likewise connected to the peritoneal cavity via a second channel. The fluid chamber and reference chamber are connected to one another via a membrane, and the membrane is connected to one end of the preloading element, the spring. By way of this connection, the preload of the preloading element is changed as soon as the membrane deflects. Here, the deflection follows the pressure difference between peritoneal cavity and reference chamber. The anti siphon shunt therefore automatically adjusts its opening pressure by way of an adaptation of a stiffness of a preloading element.

Said document however does not disclose any way of adjusting a passage, for example a gap between a barrier and a ball.

The following features of flow-reducing valves for the treatment of hydrocephalus are therefore known from the prior art:

A.) a casing having an inlet and an outlet, that

B.) comprises at least one flow path which runs through the casing,

C.) wherein the casing has a barrier and a body that can open and close the barrier.

The prior art therefore has the common disadvantage of disregarding the ventricle sizes and the state thereof. As a result, the prior art disregards the significance of a discharged drainage volume of fluid in different patients. In physiology, the so-called compliance describes the distensibility of body structure. In the field of hydrocephalus, this corresponds to the compliance of the ventricles. Since the ventricles naturally differ both in terms of their geometry and in terms of their state in a manner dependent on the patient, the compliance thereof does also. The compliance of the ventricles is proportional to their change in volume, and inversely proportional to their change in pressure. If the compliance is patient-dependent, then the pressure response in the case of an equal discharged drainage volume varies in a manner dependent on said compliance.

US 2014 0336 560 (Hakim Carlos) discloses a programmable shunt with a magnetic rotor. The rotor is connected to a cam disk. A tongue of a bending element lies on the cam disk, such that a travel of the tongue along the cam track follows a rotation/pivoting of the rotor. Because the cam track has a gradient, the tongue is raised or lowered owing to the rotation/pivoting. Because the respective height of the tongue preloads a lever that pushes a ball into its seat, a change in the preload results in an adjustment of the valve.

U.S. Pat. No. 5,167,615 has been taken as the closest prior art. Said document discloses a physiological shunt system for controlling a fluid flow from one human body part to another.

For this purpose, said shunt system comprises a casing which has two inlet channels. A closing unit, that is to say a valve, is arranged in each inlet channel.

The first closing unit is a valve plug, and the second closing unit is a flap. The plug opens the inlet channel in the presence of a particular inlet pressure. The flap permits flexible adjustment of a gap, in a manner dependent on the size of which a fluid volume can be flowed through by said gap. Because the inlet pressure is co-determined by the form of the plug, said inlet pressure is not adjustable during use, that is to say after implantation. If the gap is adjusted during use, this determines the inlet pressure of the valve.

For this purpose, the flap is mounted rotatably upstream of an open inlet channel end. Because the flap is rotationally mounted in floating fashion at its first end, its position in relation to the open inlet channel end is described by an angle between the flap and the open inlet end. If the magnitude of the angle is zero, the the inlet channel end is closed. The greater the magnitude of the angle, the further open the inlet channel end is. Because a closing and opening result from a rotation of the flap, said flap is connected by way of a member to a rotary disk, such that the rotation thereof results in an opening and closing. The connection of the member to a rotary disk is implemented by way of a bolt. The latter is inserted at its first and into the member and runs with its second end in a slot. The movement of said bolt in the slot restricts a second end of the flap, the end facing toward the inlet channel end, to one movement path. Because the rotary disk is magnetized, it can be rotated by way of a separate magnet.

By contrast to the rotational mounting of the flap, the valve plug is mounted unidirectionally in a seat. The position of said valve plug, either opened or closed, is co-determined by a pressure in the inlet channel. Said valve plug opens above a particular pressure, the valve plug opening pressure. The closing unit consequently allows a flow to pass through it. The opening pressure is also co-determined by the installation of said valve plug in the casing, because this can no longer be changed during the use of the valve, that is to say after implantation, the first valve unit is not adjustable.

A closing unit is also provided in the outlet channel of the valve. Said closing unit corresponds in terms of construction and function to the first closing unit, that is to say is also no longer adjustable during use.

Flap and valve plug, both closing units, are connected to the outlet channel of the valve.

A first disadvantage of the closest prior art is that the disclosure thereof prevents an exact setting of a drainage rate. The disclosure necessitates second closing units, two differential pressure closing units, and, arranged between these, a first, rotational closing unit with a flap. An opening and closing of the flap duly varies a volume flow through the closing unit, and thus duly influences the opening pressure, situated downstream thereof in the flow path, of the second closing unit, but does not imperatively open the latter. The setting of an intended drainage rate is therefore inexact.

This inexactness is yet further increased by a mechanism proposed by the disclosure. The mechanism comprises the rotary disk with guide slot, a bolt (cam rider) running therein, a coupling member, and a closure element (plug) which couples said coupling member. In each case two of the five members have tolerances with respect to one another, giving rise to a cumulative overall tolerance for the mechanism. Because the disclosure proposes a rotary closure as mechanism, said overall tolerance is yet further increased. Reliable running of a bolt in a slot necessitates that the slot provides, with regard to its tolerance, a compromise between running freedom and running guidance. The compromise in terms of running freedom increases the tolerance.

According to the disclosure of the closest prior art, plastic must be used for the manufacturing process. Plastic is an elastic material, owing to which it can scarcely be a basis for highly precise parts of valves. The elasticity of plastic contributes to the inexactness of the adjustment of the prior art.

A second disadvantage of the prior art lies in the risk of its disclosure. This results from possible contact of the closure member (plug) against the open end of the inlet channel. If the closure member makes contact, the inlet channel is closed. Because it is closable, a switching function is realized. Imprudent, incorrect or mistaken adjustment of the valve leads to a shutting-off of the throughflow, with the resulting consequences for patients. This risk can be visualized by considering the adjustment dimensions of the disclosure. A precise adjustment requires positioning of the flap in front of the inlet channel in the metric minimal range. Conversely, the risk results to open up the inlet channel by way of a minimal change in setting, resulting in an undesired drainage rate.

A third disadvantage of the disclosure follows from a combination of three closing units; it makes the disclosure unduly complex. All three closing units have in common the ability to serve as a switching function. The disclosure thus has triplex redundancy with regard to shutting-off. Triplex redundancy is complex, it prevents ease of understanding by a user, and thus opposes safe use.

SUMMARY

The invention is based on the problem of improving the valves. Here, the invention is based on the realization that patients react with different sensitivity to a drainage of CSF. Well-being is in some cases greatly impaired. This realization as a starting point gives rise to the demand to overcome the abovementioned disadvantages in order to further improve the control of fluid flows from one human body part to another.

The improvement is achieved by way of the features of the main claim. The subclaims describe preferred exemplary embodiments.

One advantageous embodiment of a hydrocephalus valve for draining CSF from ventricular systems of patients provides at least one casing with casing interior, which casing comprises at least one first passage for admission and/or discharging, wherein at least one body arranged in the casing interior is designed to be movable at least in one direction, and wherein at least one adjusting unit is provided. With the adjusting unit, the drainage rate in the passage can be adjusted, such that a fluid positive pressure prevailing in the ventricle in relation to a fluid pressure that is advantageous for the respective hydrocephalus patient is slowly dissipated without significantly disrupting the condition of the patient. For example, the desired fluid pressure in the ventricle may be 20 mm WC (water column) and the positive pressure may also be 20 mm WC. Limited drainage of the excess fluid then occurs.

Drainage is performed with a level of drainage performance (fluid volume per unit time). For this purpose, the drainage performance is limited to at most 1000 ml/h (milliliters per hour). The limitation is dependent on the well-being of the patient. Here, the following upper limits may also arise:

900 ml/h
800 ml/h
700 ml/h
600 ml/h
500 ml/h
400 ml/h
300 ml/h
200 ml/h
100 ml/h

The upper limit preferably amounts to 200 ml/h, even more preferably 100 ml/h and most preferably 50 ml/h.

The lower limit is likewise dependent on well-being. Furthermore, faster drainage may be demanded for medical reasons. For as long as faster drainage is not demanded for medical reasons, the lower limit is 1 ml/h preferably 1 ml/h, even more preferably at least 3 ml/h and most preferably at least 5 ml/h. Lower limits of at least 10 ml/h or 30 ml/h may also be considered. Nevertheless, the following ranges may arise for the drainage performance:

1 to 30 ml/h or 5 to 200 ml/h or 10 ml/h to 200 ml/h or 30 ml/h to 400 ml/h

The respective limits of the drainage performance are embodied in the adjusting unit.

The adjusting unit can adjust the opening so finely that the desired drainage performance is attained. The embodiments discussed below illustrate the structural details.

With the hydrocephalus valve, it is surprisingly possible to increase the well-being of patients.

The ventricular system of any person varies in terms of its size in relation to other persons. Whereas a first patient has a ventricular system of small volume, so-called slit ventricles, a second patient has a wide ventricular system.

Owing to this size variance, hydrocephalus therapy of both patients using an identical hydrocephalus valve has different consequences. Drainage of a defined fluid volume, for example of one drop, results in a different change in pressure in the ventricular system of both patients. If drainage, for example of a small fluid volume, is significant for a patient with a small-volume ventricular system—that patient feels discomfort—, the same drainage is insignificant for a patient with a large-volume ventricular system.

In summary, the invention thus permits patient-specific individual adjustment of drainage or of the rate thereof.

Optionally, a drainage facility is equipped exclusively with the above adjustment facility. The drainage performance is then preferably selected such that, by contrast to conventional drainage facilities, constant drainage is performed. At the same time, excessive drainage is however prevented. Droplet drainage is then realized. For this purpose, excessive drainage is however prevented. Droplet drainage is then realized. For this purpose, it is for example possible for the fluid volume accumulating per unit of time to be determined in that the excess fluid is initially extracted to the outside over a relatively long period of time (several days) and can be determined using a measuring vessel.

Subsequently, from the collected fluid quantity, a mean fluid accumulation/drainage quantity per unit of time can be determined. The value may then be adopted in the valve adjustment.

Alternatively, such an adjustment may be performed during the course of approximation tests with measurement of the ventricular pressure. Here, the patient is accompanied with pressure measurements and the adjustments to the valve are varied until a normal pressure has become established in the ventricle.

The valve bodies that are moved for the adjustment of the drainage may be moved both rectilinearly and on a curved path.

A rectilinear movement of the valve body preferably occurs.

In another advantageous exemplary embodiment, at least one hydrocephalus valve is combined after with at least one second valve which is connected downstream or upstream the hydrocephalus valve. Here, one valve may be a conventional valve with an "open" and "closed" function. The first valve then has the task of preventing excessive drainage. The second valve may then concentrate on the limitation of the throughflow.

Here, both valves may be arranged in one casing or may have separate casings.

A valve combination increases the chances of successful treatment because it permits an adaptation of a combination of the valve with the hydrocephalus valve to the respective usage situation. The valve combination thus yields the advantage of being able to react flexibly to the treatment requirements of a patient.

What is preferable for the valves is the principle of a body in an (opening) gap. The principle of the invention fluid can enter the gap in a flow-optimized manner.

The improved fluid guidance also safeguards against deposits.

The hydrocephalus valve may for example be combined with a gravitational valve. The gravitational valve has a closing part, normally a ball, which, in the standing position of the patient, owing to a corresponding arrangement in the patient, closes the drainage line under the weight of the closing part. In the recumbent position of the patient, the valve opens already in the presence of a low fluid pressure, which displaces the closing part into the open position. Such valves open fully or close fully.

Also known are gravitational valves with two balls, one of which is small and the other of which is large. The smaller ball effects the sealing in the valve seat in the closed position. The large ball serves for increasing the weight in the closed position.

The hydrocephalus valve is also combinable with at least one differential pressure valve. In this case, the differential pressure valve may be regarded as a switch. The adjustable differential pressure valves commonly have a spring-loaded closing part, normally a spring-loaded ball. In the event of a particular fluid pressure being exceeded, the closing part opens. The opening increases in size with increasing pressure counter to the resistance of the spring that exerts load on the closing part. In the recumbent position, the fluid pressure is at its greatest; accordingly, the opening and the drainage are at their greatest. In the standing position, the fluid pressure is at its lowest, and accordingly the valve opening is at its smallest. Differential pressure valves have the advantage of a continuously variable adaptation to intermediate pressures in positions between the standing position and the recumbent position. The adjustability of such valves furthermore has the advantage of the adaptation to different drainage requirements. Different drainage requirements in the case of different patients are normal. However, even in the case of an individual person, a change in the setting arises. This is generally the case after implantation until the correct drainage for the clinical picture has been found.

The valve combination may also comprise a multiplicity of valves. In the combination of a gravitational valve with a differential pressure valve, the differential pressure valve performs its function in the recumbent position. In the recumbent position, the gravitational valve is open. In that situation, the differential pressure valve regulates the drainage. The gravitational valve may, in the combination of the two valves, be positioned upstream or downstream of the other valve in a flow direction of the fluid in the casing.

The valve is preferably, after an adjustment, secured in the respective position in order that no inadvertent adjustment can occur. A suitable securing facility is formed by a brake which is released prior to every adjustment and which automatically assumes the braking position/securing position after a change in the setting. This yields the following steps that occur during the adjustment: passing at least one magnet over the hydrocephalus valve; releasing a brake of an adjusting unit of the hydrocephalus valve; rotating the adjusting unit such that the body is arranged in an intended position in the gap in the hydrocephalus valve.

Because the body can be moved into an intended position, the method offers the advantage of adjusting the drainage rate. Through this adjustability, the pressure change in the ventricular system of each patient can be set independently of the condition of the ventricular system. If two patients have different ventricle sizes, it is possible by way of different setting, that is to say positioning, of the body in the passage to set a different drainage rate, such that the pressure responses in the ventricular systems of the patients are equal. Irrespective of the ventricle sizes, the invention thus makes it possible to set one, that is to say the same, pressure response for different patients.

The body is preferably arranged in at least one first passage. Here, different bodies may be used, for example:
 body with a larger diameter than the passage
 body with a smaller diameter than the passage
 body with a rounded portion at the end facing toward the passage
 body with a conical tip at the end facing toward the passage
 body with a wedge-shaped tip at the end facing toward the passage
 plug-like body
 rod-like body with round and/or polygonal cross sections
 profile-like body with indentations and/or protuberances in the cross section Use is preferably made of a body with a conical tip and a smaller diameter than the passage.

The bodies may correspond to different passage openings, for example:
 at the area of contact with the body, sharp-edged and/or rounded and/or smooth openings
 conically widening openings
 wedge-shaped widening openings
 openings without an area of contact with the body
 openings with guides for the body If the body is smaller in terms of its dimensions than the passage, at least one gap is formed between them. This gap formation can also be utilized for the setting according to the invention.

In a further advantageous embodiment, as a body, use is made of at least one guided plug, wedge, cone, profiled bar or a ball.

Different levels of fluid accumulation may optionally result in different geometries on the body and on the associated passage opening. Accordingly, for example, for low levels of fluid accumulation, geometries of the body and passage opening are particularly suitable in the case of which the body movement If a cylindrical profiled bar is provided as body, that is to say as closing part, and if this issues with a conical tip into a casing bore, this advantageously results in a precisely adjustable closure mechanism. In this case, the conical tip in interaction with the casing bore defines an opening cross section, which is definitive of the drainage flow, of the casing bore.

It is advantageous if the longitudinal axis of the cylindrical profiled bar is aligned with the central axis of the casing bore that forms the inlet or outlet. Inserts for the inlet and/or outlet are optionally provided in the casing. The bores for the inlet and/or outlet are then provided in the insert.

The body preferably has a collar, wherein, between the collar and at least one surface portion of the adjusting unit, there is provided a spring which ensures permanent contact of the body with the surface portion. Adjustability of the invention over time is realized by way of this assurance.

The collar advantageously supports the spring such that the spring force thereof seeks to push the body, for example a needle, out of a bore. Collar and spring thus assist a principle, the aim of which is to keep the invention in an open state at all times. By way of this principle, a risk of undesired closure is avoided. If a valve closes in an undesired manner, no further fluid is drained, and the symptoms of hydrocephalus remain untreated.

It is furthermore advantageous if more than one adjustable body is arranged in the passage, for example one body at the inlet and one body at the outlet. Use may also be made of valve bodies in a so-called parallel configuration. If the two bodies can thus be of small design, even smaller than a single body which imparts an identical action thereto, the structural volume of the valve inlets and outlets can be made smaller, such that the valve structural volume is reduced in size.

It is advantageous if the passage is at least one first valve outlet, which prevents a build-up of fluid within the casing. If the passage is a first valve outlet, that is to say if the body is seated in a valve outlet, and body and valve outlet form a permanent gap, the invention is permanently open at the side of the outlet. Fluid is consequently permanently drained, the build-up of which fluid is prevented.

It is furthermore advantageous if the adjusting unit comprises or is a cam disk. Then, an actuating device, the adjusting unit, is formed, the actuating variable of which is the cam profile. If the cam disk is formed from a durable material such as titanium, the result is a durable actuating device. The durability thereof advantageously satisfies the requirement for one-off implantation. Multiple implantation is, with high probability, avoided.

In a particularly advantageous embodiment, the cam disk is a rotor.

The rotor/cam disk may be of stepped design. Said rotor/cam disk thus has a multiplicity of cam tracks. Each cam track may be used for controlling different valves. A first closing part for closing the valve against the inlet opening or outlet opening may be controlled by way of a first cam track. A second closing part may be controlled by way of a second cam track.

The cam disk, a rotor, advantageously has protuberances and indentations. Opening-up and shutting-off are achieved by way of corresponding protuberances and indentations of the rotor/cam disk. Here, the protuberance pushes a ball out of a seat. The indentation provides the seat for a ball. The function of a switch is thus advantageously achieved.

Stepped switching, that is to say opening-up, is selectively also provided. The switching steps may involve a step opening of the valve. It is thus possible, even in the case of relatively large drainage lines with an inherently relatively large fluid flow, to maintain a relatively small fluid flow.

In the case of a rotor/cam disk being used as an adjusting device for the gravitational valve, it is possible, in the case of a combination with a second valve in the common casing, to realize a combination with a further cam disk or a rotor, if the second valve is also adjustable by way of a rotor/cam disk. It is advantageous for the two rotors/cam disks to then be adjusted jointly. Suitable for the adjustment are inter alia the known magnets in the rotor/cam disk in conjunction with known adjusting devices, which are placed onto the skin of the patient over the casing and which in turn are equipped with magnets, such that, by way of a rotation of the adjusting device, the rotors/cam disks can be pivoted.

It may be advantageous for each of the rotors/cam disks to be produced separately and adapted to the requirements of the patient and subsequently connected to one another in the correct position relative to one another in order for both rotors/cam disks to be adjusted jointly. Here, the region of the indentation in the cam disk/rotor belonging to the gravitational valve determines the activation of the gravitational valve and the drainage of the fluid. The second valve should impart its action within this range. Therefore, the cam disk belonging to the second valve should assume the desired position in relation to the second valve.

A preferred embodiment is characterized in that the cam disk has an axis, wherein the axis is arranged in front of the passage.

As a result of the positioning of the center of rotation of the rotor or of a cam disk in front of the passage, imbalanced running of the rotor is avoided. This is yet further improved if the axis of rotation lies on the axis of symmetry of a passage. Because no imbalance, a spacing between axis of symmetry and axis of rotation, is present, the body is guided in a precise manner, that is to say in parallel, in the passage by way of the cam track of the cam disk or of the rotor.

The adjusting unit preferably comprises at least one rotor. The rotor is be regarded a rotatable/pivotable part of a hydrocephalus valve. The rotors may have different forms: round, or have the form of a disk, of a partial disk, of a screw, of a partial screw or of a thread.

It is furthermore advantageous if the adjusting unit or the rotor comprises at least one magnet. Magnetic forces pass through the skin of patients. It is advantageously then possible for the rotor of the adjusting unit to be rotated or pivoted by way of a tool which likewise has at least one magnet.

It is advantageously also possible in this way for pivot arms, levers, springs and also the body of the adjusting unit to be moved with the rotor. The movement of the adjusting unit preferably comprises a partial rotation and/or one rotation and/or a number of rotations and/or pivoting movements or a sliding movement and/or a stroke movement. The body of the adjusting unit can thus be adjusted in a precise manner. The precision thereof advantageously increases if a partial rotation or rotation of the adjusting unit is converted into a linear movement of the body. By way of this conversion, it is possible for partial rotations or rotations or pivoting movements of the adjusting unit, which are comfortable for a person to perform, to be converted into precise linear movements.

It is furthermore advantageous if the adjusting unit controls the movement of the body along a cam track. Cam-track control arrangements are durable and can be produced precisely and easily.

In a further advantageous embodiment, the cam track is formed by the circumferential surface or the face surface of the adjusting unit or of the rotor. In this way, partial rotations or rotations and pivoting movements of the adjusting unit can be transmitted easily and in uncomplicated fashion to other mechanism members.

The body, that is to say the closing part of the outflow-side valve, preferably bears under spring pressure against the cam track. In this way, an instantaneous adjustment is possible; any change in the cam track results in a change in the position of the body in the gap.

It is furthermore advantageous if the body bears at its first end against the cam track. In this way, play between body and cam track is prevented. Any change in a setting is immediately transferred to the body.

In a further advantageous embodiment, the body bears at its first end with a rounded portion against the cam track. Rounded portions can easily slide along on a cam track, such that the profile of the cam track can advantageously be transferred with little friction to the rounded portion.

It is preferable for a body in the form of a profiled rod to project with a tip into an opening of the outlet, wherein the tip is preferably conical, and even more preferably the outer diameter of the profiled rod is greater than the opening width of the outlet.

It is furthermore advantageous if the outlet has a tubular form with a cylindrical inner shell. This can be manufactured easily and precisely.

In a further advantageous embodiment, the outlet is formed by an insert of the casing, and the guide for the body is formed by the insert of the casing. Inserts can be provided and stocked, and made available during an implantation, for different embodiments of inlets and outlets. In this way, it is possible, as necessary, to decide during the implantation what body and what inlet or outlet dimensions must be used. By way of different inserts in interaction with different inlets or outlets, it is possible for each patient to be treated individually.

The body is preferably supported at its first end in the insert. This provides a holding action for said body.

In a further advantageous embodiment of the combination of the hydrocephalus valve with a further valve, both valves are arranged in one flow path.

Because they are situated in one flow path, a common pressure prevails across them. This has the advantage of easier coordination of the valves. By contrast to the closest prior art, the novel valve is uncomplicated and is easy for users to understand. A flow channel requires merely the manufacture thereof; this reduces outlay and production errors.

Furthermore, numerous flow-calmed zones are avoided. This has the advantage that no deposits can form there. In an advantageous embodiment, the second valve of the valve combination is a differential pressure valve. In this way, the functionality of the valve combination can be limited by a lower or upper threshold value.

In a further advantageous embodiment, the second valve is a spring-loaded closing part, which closes and opens in a manner dependent on the fluid pressure.

In the case of a gravitational valve being used as second valve, this is preferably formed by at least one ball, optionally by two balls. The second valve may also have a rotor/cam disk, which are in direct contact with the ball that forms the closing part or with a ball that forms an additional weight and which push the ball which forms as closing part into the valve seat thereof. In the case of common materials being used for ball, valve seat and rotor/cam disk, significant wear is not to be expected on the ball or on the rotor/cam disk or in the valve seat. If wear nevertheless poses a problem, it is possible for wear-resistant materials such as titanium to be selected for the ball, valve seat and/or rotor/cam disk. Even a small leakage flow between ball and valve seat owing to required play is generally not detrimental. If a small leakage flow nevertheless poses a problem, it is for example possible for the valve seat to be designed to be flexible. In addition to or instead of a flexible valve seat, it is also possible for the sliding surface to be designed to be flexible. Even a small degree of flexibility reduces possible leakage flows. With the flexibility, in the presence of the corresponding pressure of the valve ball in the valve seat, leakage flows can also be prevented.

It is advantageous, if a common casing is provided for both valves, if only said one casing then needs to be inserted during an implantation. This saves outlay. If the casing is of modular construction, it is possible for the casing to be pre-configured, in a manner dependent on the ventricle size of the patient, long before being implanted. For example, by contrast to the prior art, it is possible for individual inserts to be used for individual inlets or outlets and/or bodies, rotors. On-site assembly at remote locations is also made possible, such that different patient groups such as children or elderly persons can be treated using adapted valves.

Particularly advantageous is the combination of multiple valves in one casing, preferably of a gravitational valve with a differential pressure valve or some other valve in a common casing. This facilitates the implantation process. A line piece between the two valves of the earlier proposal is thus omitted. With the combination of both valves in a single casing, the structural outlay is reduced. Furthermore, the casing offers the possibility of expedient configuration of the connection of the two valves. The connection is formed by channels. The channel cross section may be selected to be greater in the valve casing than in the case of a connecting line of the earlier proposal.

Furthermore, the transition from one valve to the connecting channel and from the connecting channel to the other valve (for example from the gravitational valve to the connecting channel and from the connecting channel to the differential pressure valve) can be designed in a more flow-optimized manner. This is manifest in a lower flow resistance than in the case of a connection of the two valves by way of a line for feeding fluid to the common casing and/or for discharging fluid.

It is furthermore advantageous if, in the casing, the hydrocephalus valve is assigned to the inlet and the second valve is assigned to the outlet, or the second valve is assigned to the inlet and the hydrocephalus valve is assigned to the outlet, and that, in the casing, channels are provided from the hydrocephalus valve to the second valve, which channels have a lower flow resistance than a connection of the two valves to a drainage line as are provided for the feed of fluid to the common casing and/or for the drainage of fluid from the common casing.

Preferred embodiments of the invention will be discussed by way of example on the basis of a drawing. Specifically, in the figures of the drawing:

BRIEF DESCRIPTION OF THE DRAWINGS

FIG. 1 shows an exemplary first embodiment of a hydrocephalus valve in a schematic view from above.

FIG. 1a shows a detail of FIG. 1.

FIG. 1b shows a further detail of FIG. 1.

FIG. 2 (composed of FIGS. 2a and 2b) shows details of a preferred embodiment.

FIG. 3 (composed of FIGS. 3a, 3b, 3c, 3d) shows details.

FIG. 10 shows a preferred, second embodiment of a hydrocephalus valve.

FIG. 11 shows a further embodiment of a hydrocephalus valve in a schematic illustration.

FIG. 12 shows a further embodiment of a hydrocephalus valve in a schematic illustration.

FIG. 13 shows a further embodiment of a hydrocephalus valve in a schematic illustration.

FIG. 18 shows a preferred embodiment of a rotor in a plan view.

DETAILED DESCRIPTION

Figure 2A:
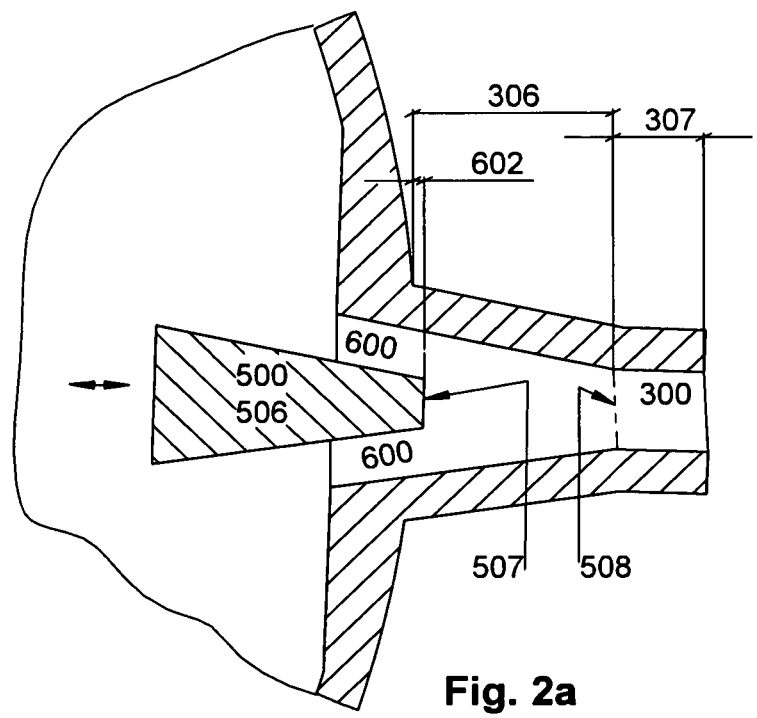
FIG. 2a shows a detail with a preferred embodiment of a body with a gap.

FIG. 1 shows a hydrocephalus valve 100 in terms of its construction in a schematic view from above. Said figure shows a construction with a casing 200, in which an adjusting unit 700 in the form of a cam disk 704, a coupling element 400 and a body 500 are mounted. The casing furthermore comprises an inlet 202 and an outlet 203.

The movement of the cam disk 704 is positively guided in the casing interior 201 centrally by an axle 705, whereas the body 500 is guided not by way of its drilled-out body axis 502 but by way of its body lateral surface 503. FIG. 1 shows that the body 500 is formed as a wedge, such that its body lateral surface 503 tapers from a first body end 504 in the direction of a second body end 505. FIG. 1 likewise shows that the shape of the passage 300 is of wedge-shaped or cup-shaped form in cross section. By virtue of the tapering of the body lateral surface 503 corresponding to the tapering of the passage, the wedge 506 is guided in the passage 300 along its body surface.

The coupling element 400 is arranged with its first end 401 on the wedge 506 and with its second end 402 against the cam disk 704. The coupling element 400 may expediently be rigid or elastic. FIG. 1 shows an embodiment with a rigid coupling element 400. This may be a pin or a plate. Here, the cross section through the pin may be round, elliptical or polygonal. In the present embodiment, the pin may be a round metal or polygonal metal part composed of titanium. It may however alternatively also be manufactured from high-grade steel, a thermoset or a thermoplastic. By virtue of the coupling element 400 being connected to the cam disk 704 and to the wedge 506, a movement of the cam disk 704 guides the movement of the wedge 506.

The movement of the wedge 506 in the passage 300 results in a gap 600 between the lateral surface of the wedge 506 and the passage inner surface 304 of the passage 300. The further the wedge 506 is moved into the passage 300 in the passage direction 302, the longer the gap 600 becomes. With increasing gap length 602, the gap inner surface thereof increases in size. The gap inner surface is made up of the lateral surface of the wedge 506 and the passage inner surface 304 from the start of the gap to the end thereof. The larger the gap inner surface is, and the narrower the gap is, the greater is the friction of a fluid 900 which is intended to pass through, or which passes through the gap 600, with the gap inner surface. The lateral surface of the wedge 506 thus acts as a flow resistance, that is to say also the wedge 506. Because the position of the wedge 506 is adjustable by way of its movement in the gap 600 by way of the cam disk 704 via the coupling element 400, the flow resistance is also adjustable. Consequently, the flow resistance of the hydrocephalus valve 100 is adjustable owing to the adjustability of the gap length.

The throughflow quantity of the fluid per unit of time is adjusted by way of the flow resistance.

A movable arrangement of the body 500 in the first passage direction 302 permits different, advantageous variants for producing a gap 600. This may mean that an angle exists between a movement direction of the body 500 and the movement of said body along a positive guide, which is determined for example by a linear bearing 405. The angle between the main movement direction of the body and the first passage direction 302 is, in other exemplary embodiments, less than 80°, preferably less than 50°, in particular less than 20° or even smaller, that is to say amounts to less than 5°. In the exemplary embodiment, the angle is 0 degrees. Thus, the main movement direction of the body 500 is coaxial with respect to the passage direction 302, and a symmetrical gap 600 is formed as soon as the body 500 is spaced apart from the passage 300. In the exemplary embodiment, those portions of the body 500 and of the passage 300 which face toward one another are symmetrical. Alternatively to the gap length 602 and/or in addition, other geometrical features of a body 500 can be changed in order to vary a flow resistance through the passage 300. In a further embodiment, the roughness of the lateral surface of the wedge 506, or the profile thereof, may be varied.

In a preferred embodiment, a spring seat 800 is formed into an edge of the passage 300. Here, the spring seat 800 may be a pin to which a spring 802, for example a spiral spring, can be mounted. The secure seat of a spring 802 promotes the positioning thereof between an edge of the passage 300 and the wedge 506, such that the spring force of the spring 802 pushes the wedge 506 out of the passage 300 in the direction of the passage end 301.

Owing to the rotation or pivoting movement of the cam disk 704 and the consequential movement of the body 500, the spacing 702 between a center of rotation of the cam disk 704 and a reference point of the body 500 varies.

Aside from cam disks 704, alternatively other adjusting units may be used which, in terms of their direction 701, are also movable in translation.

FIG. 1a shows a detail view from FIG. 1, which illustrates two alternatives of a coupling element 400.

FIG. 1b shows a detail view from FIG. 1, which illustrates an opening state of the hydrocephalus valve 100 (spring 802 not illustrated). In the open state, the second body end 505 coincides with the cross-sectional area 303.

FIG. 2a shows a detail with a preferred embodiment of a body with a gap. The preferred embodiment is based on the interaction of two components, a passage 300 and a body 500. FIG. 2a shows that the passage 300 is composed of a funnel-shaped inlet region 306 a hose-like portion 307. FIG. 2a also shows that a gap 600 exists between the two components if the body 500 has been produced as a wedge 506. For this purpose, the wedge 506 may for example be formed out of a titanium, steel or biocompatible elastomer block. In the preferred embodiment, the wedge 506 has been milled from a titanium block. It can however alternatively also have been cut out of a biocompatible plastics block. A movement of the wedge 506 into or out of the funnel-shaped inlet 306 of the passage 300 varies the gap length 602 and thus the flow resistance between wedge 506 and passage 300. In a preferred embodiment, the wedge 506 seals against the passage 300 if the encircling edge of the wedge face surface 507 abuts against the transition edge 508 between funnel-shaped inlet 306 and hose-like in the portion 307.

Figure 2B:
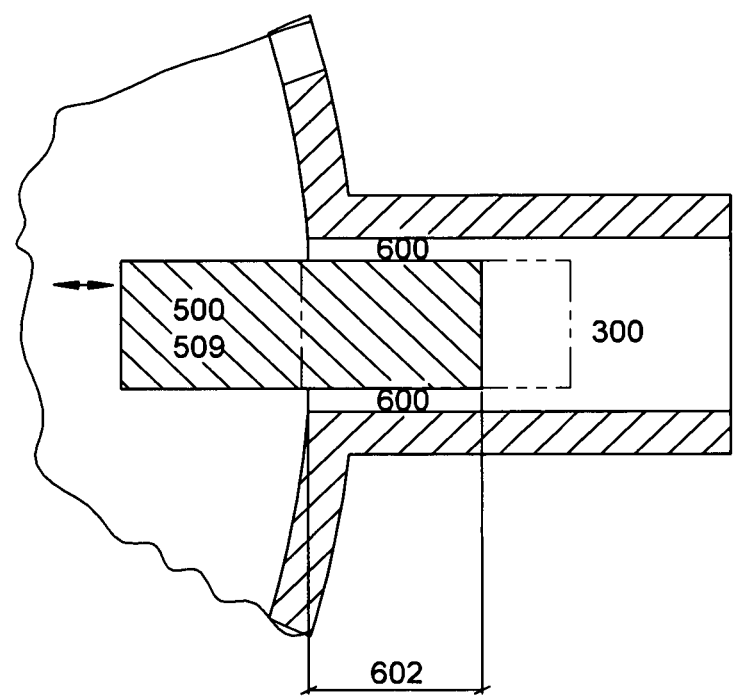
FIG. 2b shows a detail with an alternative embodiment of a body with a gap.

FIG. 2b shows a detail with an alternative embodiment of a body with a gap. The body 500 has the form of a rod 509. The greater the gap length 602 and the smaller the gap width, the greater is the flow resistance between rod 509 and passage 300. The pushing-in of a rod 509 with a great length thus results in an increase in the flow resistance. If the rod 509 is pushed deep enough into the passage 300, this results in an infinitely high flow resistance. In the present embodiment, the length of the rod 509, that is to say the maximum level of the flow resistance, has been adapted to the position-dependent weight force of a volume of CSF in the Earth's gravitational field. Alternatively, the body 500 may be a ball (not illustrated), a cone (not illustrated) or a cylinder (not illustrated).

Figure 3A:
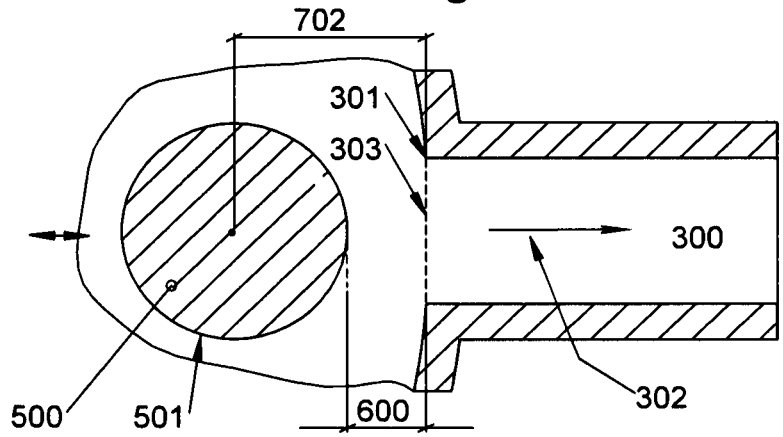
FIG. 3a shows a detail with an alternative embodiment of a body with a gap.

FIG. 3a shows a detail with an alternative embodiment of a body with a gap, in the case of which a gap 600 can be produced between an outer edge of a spherical body 500, such as for example a ball, and a bore. For this purpose, the ball is positioned with a spacing 702 in front of the bore. The bore acts as a passage 300, and the spacing between outer edge and bore edge forms the gap 600. In a manner dependent on the spacing 702, the passage volume thereof varies.

Figure 3B:
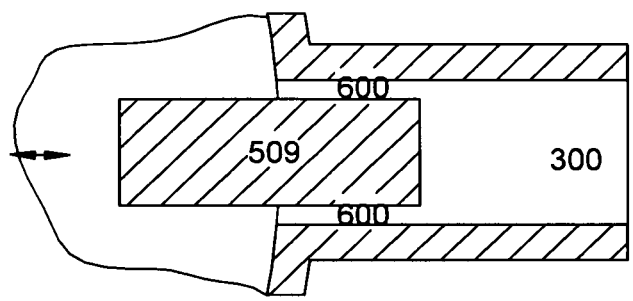
FIG. 3b shows a detail with an alternative embodiment of a body with a gap.

FIG. 3b shows a detail with an alternative embodiment of a body with a gap, wherein a gap 600 between a rod 509 and a bore forms the passage 300.

Figure 3C:
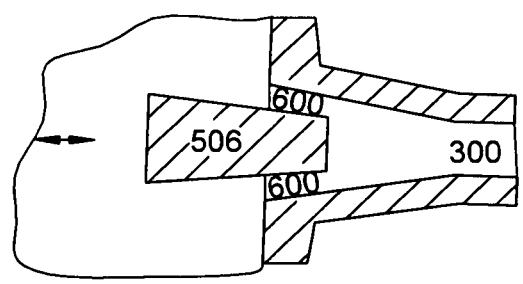
FIG. 3c shows a detail with an alternative embodiment of a body with a gap.

FIG. 3c shows a detail with an alternative embodiment of a body with a gap 600, which is produced between a wedge 506 and a passage bore 300.

Figure 3D:
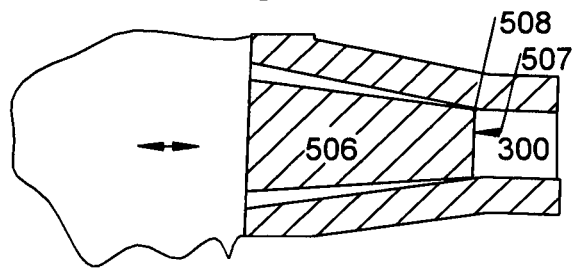
FIG. 3d shows a detail with an alternative embodiment of a body in a gap.

FIG. 3d shows the exemplary embodiment from FIG. 3c in a closure state. The encircling edge of the wedge face surface 507 of a wedge 506 seals against the transition edge 508 of a passage 300 between funnel-shaped inlet and hose-like portion.

Figure 4:
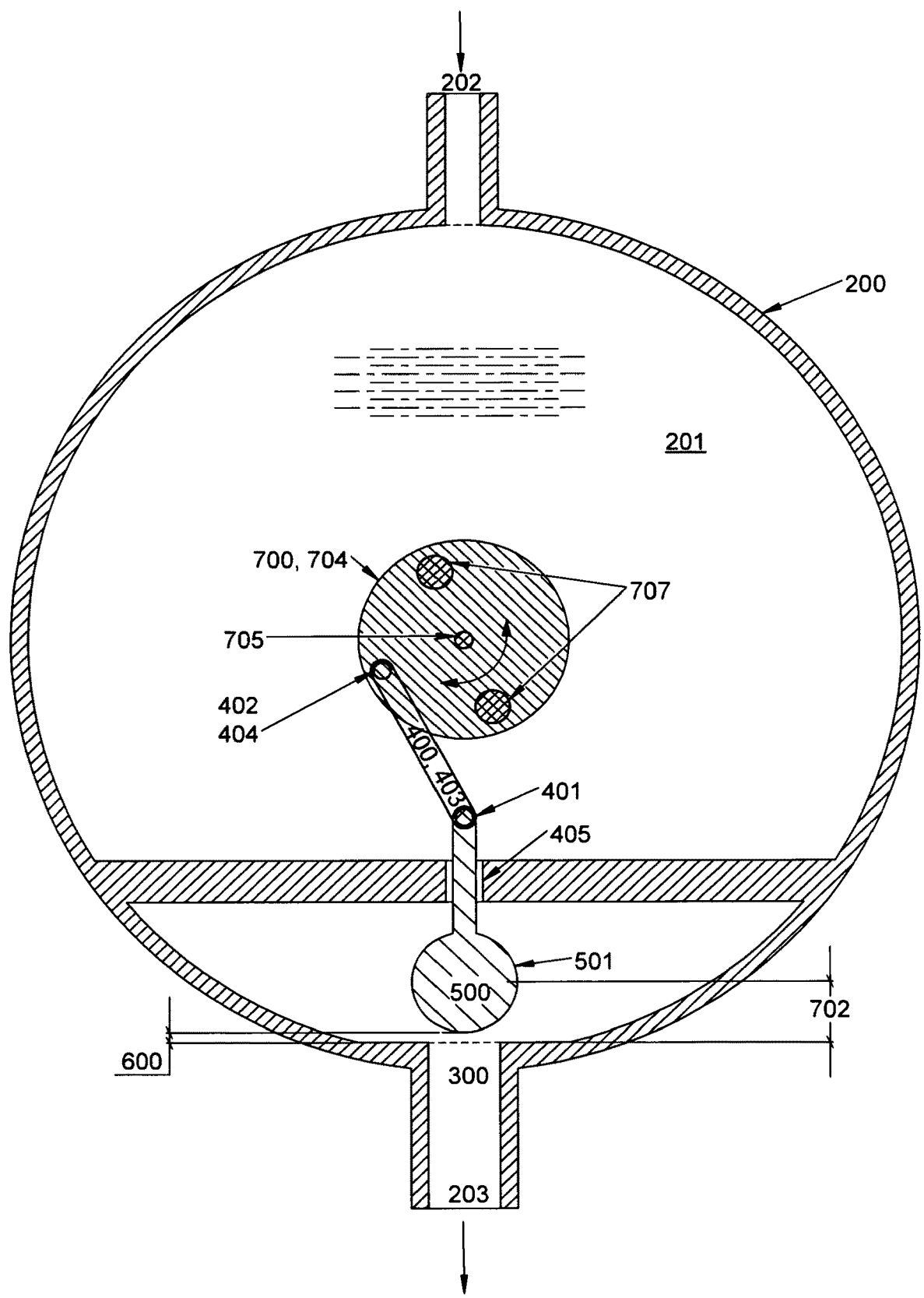
FIG. 4 shows an alternative, second embodiment of a hydrocephalus valve in a side view.

FIG. 4 shows an alternative, second embodiment of the invention in a side view. In this, in the casing interior 201 of a casing 200 with inlet 202 and outlet 203, a cam disk 704 and a body 500 are connected by way of a coupling element 400 in order to convert a rotation or a partial rotation of the cam disk 704 into a decrease or increase of the spacing 702. This variation corresponds to an adjustment of the gap 600 and, in association with this, to an adjustment of the passage volume. For this purpose, the cam disk 704 is mounted on an axle 705.

For this purpose, a mechanism member 403, for example a mechanism rod, is attached at at least two different ends in each case to the cam disk 704 and to the body 500. In the present embodiment, the mechanism member 403 is, by way of a journal 404 at the second end 402 thereof, connected to the cam disk 704 in the vicinity of the outer edge thereof. By contrast, the other end, the first end 401 of the mechanism member 403, that has a passage bore, is mounted in a jaw of the body 500.

For guidance of the body 500, the latter is mounted in a linear bearing 405.

By virtue of the fact that an adjusting unit 700, in the present embodiment at least one magnet 707, is embedded into the cam disk 704, it is possible by way of a magnetic coupling between the cam disk 704 and an adjusting tool (not illustrated) for the cam disk 704 to be rotated, that is to say adjusted. By way of the conversion of this rotation into a defined spacing 702 between body 500 and passage 300, the flow resistance, that is to say the size of the gap 600 or the passage volume thereof, can be adjusted, such that the drainage volume of the hydrocephalus valve 100, that is to say the setpoint outflow of a volume of CSF, is made adjustable.

Figure 5:
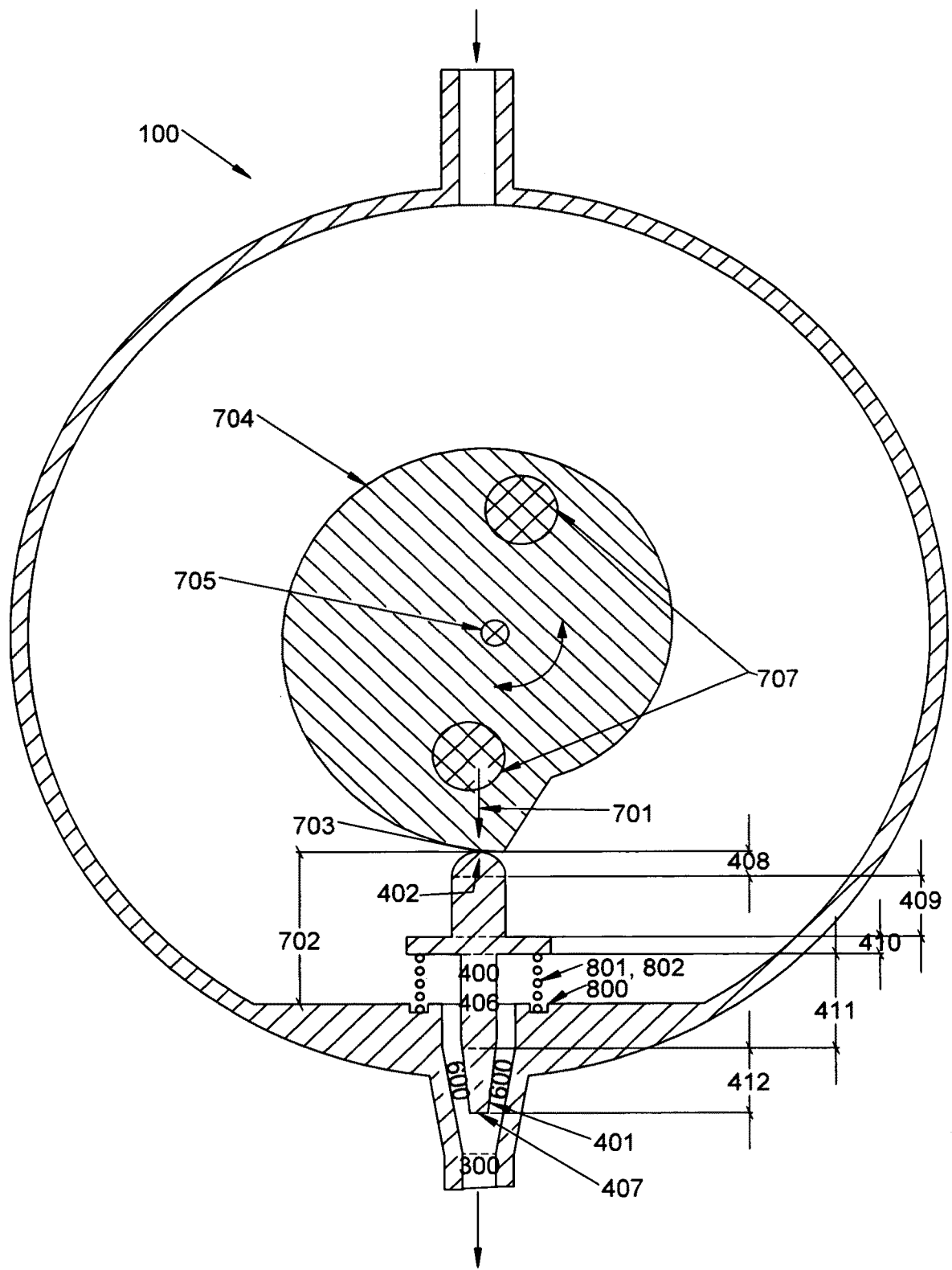
FIG. 5 shows an alternative, third embodiment of a hydrocephalus valve in a side view.

FIG. 5 shows an alternative, third embodiment of the invention in a side view. In this embodiment, the hydrocephalus valve 100 comprises a cam disk 704 with an axle 705, a plug 406, a linear bearing 405, a spring 802 or some other desired spring element 801 and a passage 300. For this purpose, the spring 802 or the spring element are mounted in a spring seat 800. In terms of principle, in this embodiment, a rotation of the cam disk 704 is, by way of a contact point 703 between cam disk 704 and plug 406, transmitted to the latter in the linear movement thereof. The plug 406 is, during its movement, pressed by the spring against the cam disk. To ensure that the closure end 407 of the plug 406 slides reliably into and out of the passage 300 or the passage end thereof, the plug 406 may be mounted by way of a linear bearing 405. In a preferred embodiment, the plug 406 is mounted in one of its uniform portions. For this purpose, the plug 406 is formed from a material block, in particular a titanium block, by turning. Turning simplifies production of the plug 406 with five main portions, a contact portion 408, a neck portion 409, a collar portion 410, an elongation portion 411 and a closure portion 412. The spring 802 is mounted in a spring seat 800, which is formed as a ring. By way of the movement of the plug 406, for example in the form of a needle 1152, a gap 600 or a gap passage 1154 or a gap-like passage is generated.

Figure 6:
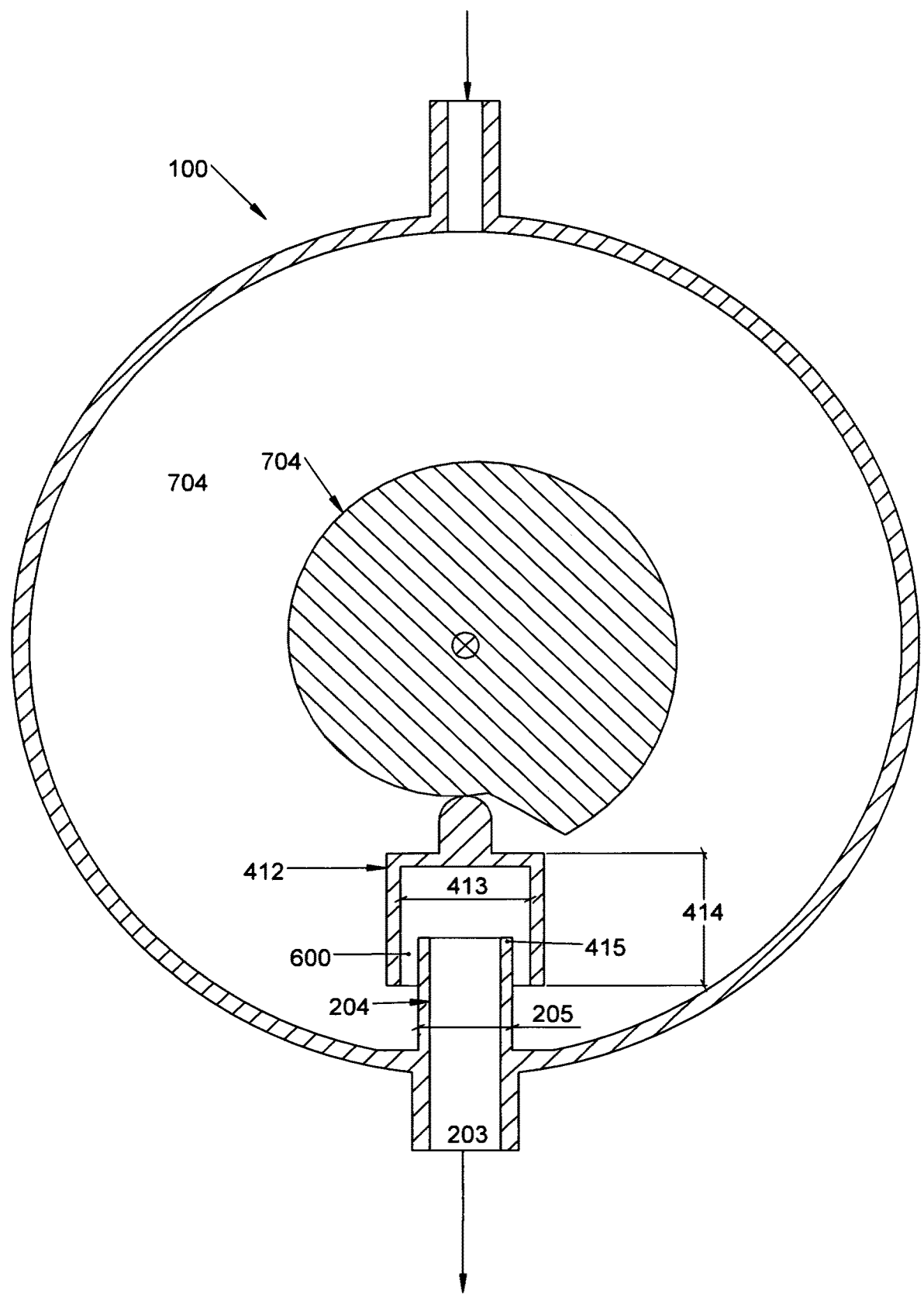
FIG. 6 shows an alternative, fourth embodiment of a hydrocephalus valve in a view from above.
Figure 7:
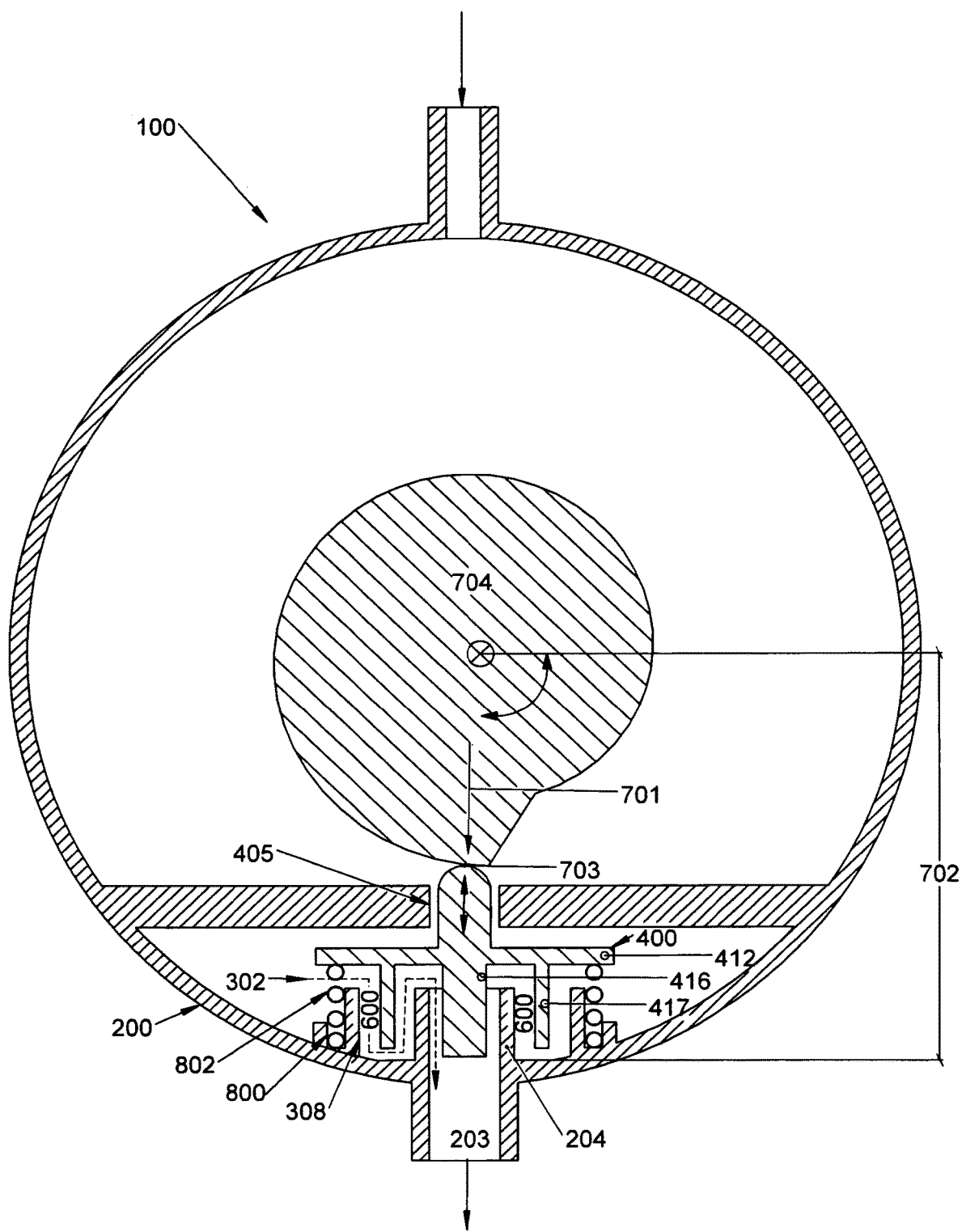
FIG. 7 shows an alternative, fifth embodiment of a hydrocephalus valve in a side view.

FIG. 6 shows an alternative, fourth embodiment of the invention in a view from above. Here, the illustrated hydrocephalus valve 100 comprises not only a cam disk 704 but also a sleeve 412 and an elongate outlet 203 in the form of a pipe 204. The pipe 204 may be a small pipe, a hose piece, a hose end, a pipe portion or a flexible or rigid hollow body. In a further embodiment, the sleeve inner diameter 413 approximately corresponds to the pipe outer diameter 205. For a first embodiment, the correspondence means: the sleeve inner diameter 413 has the same dimension as the outer diameter 205 plus a required movement clearance for a movement of the closure portion 412 on the pipe 204. In a preferred embodiment, the diameters differ from one another to a greater extent, such that a gap 600 is formed between the sleeve 412 and the pipe 204. The pipe 204 runs with a first pipe end 415 in the sleeve 412. FIG. 7 shows a hydrocephalus valve 100 with a coupling element 400 of telescopic design in a side view, which is preferably based on the embodiment in FIG. 6. In the further, telescopic embodiment, the sleeve 412 is likewise formed, specifically milled, from a titanium block, but a central plug 416 and an edge 417 have been milled out. In addition to an elongate outlet 203 in the form of a bushing 204, a round outlet bushing 308 has been formed in the casing 200 coaxially with respect to the passage 203. Alternatively, the outlet bushing 308 may also, coaxially with respect to the passage 203, be adhesively bonded, plugged, screwed, pressed or fused in the casing 200, on the casing 200 or, by way of holding elements, within the passage 300. In a further embodiment, the outlet bushing 308 is manufactured as a single piece from the casing 200, a casing cover or a casing pot. The sleeve 412 is supplementarily guided in a linear bearing 405. The tip of a sleeve end makes contact, at a contact point 703 or in a contact line or over a contact area, with the outer edge of the cam disk 705. In this embodiment, a spring 802 is a compression spring, such that it pushes the sleeve 412 out of the outlet 203, such that a gap 600 results between the central plug 416 and the pipe 204 and between the edge 417 and the pipe 204 and between the edge 417 and the outlet bushing 308. The spacing 702 between the cam disk 704 and the end of the coupling element describes the adjustability of the gap 600, or the gap passage, as a possible adjustment parameter. The adjustability can thus be mathematically described by presenting the relationship between rotation of the cam disk 704 in its direction of rotation 701 and the change in the spacing 702.

The spring 802 is mounted in a spring seat 800.

Figure 8:
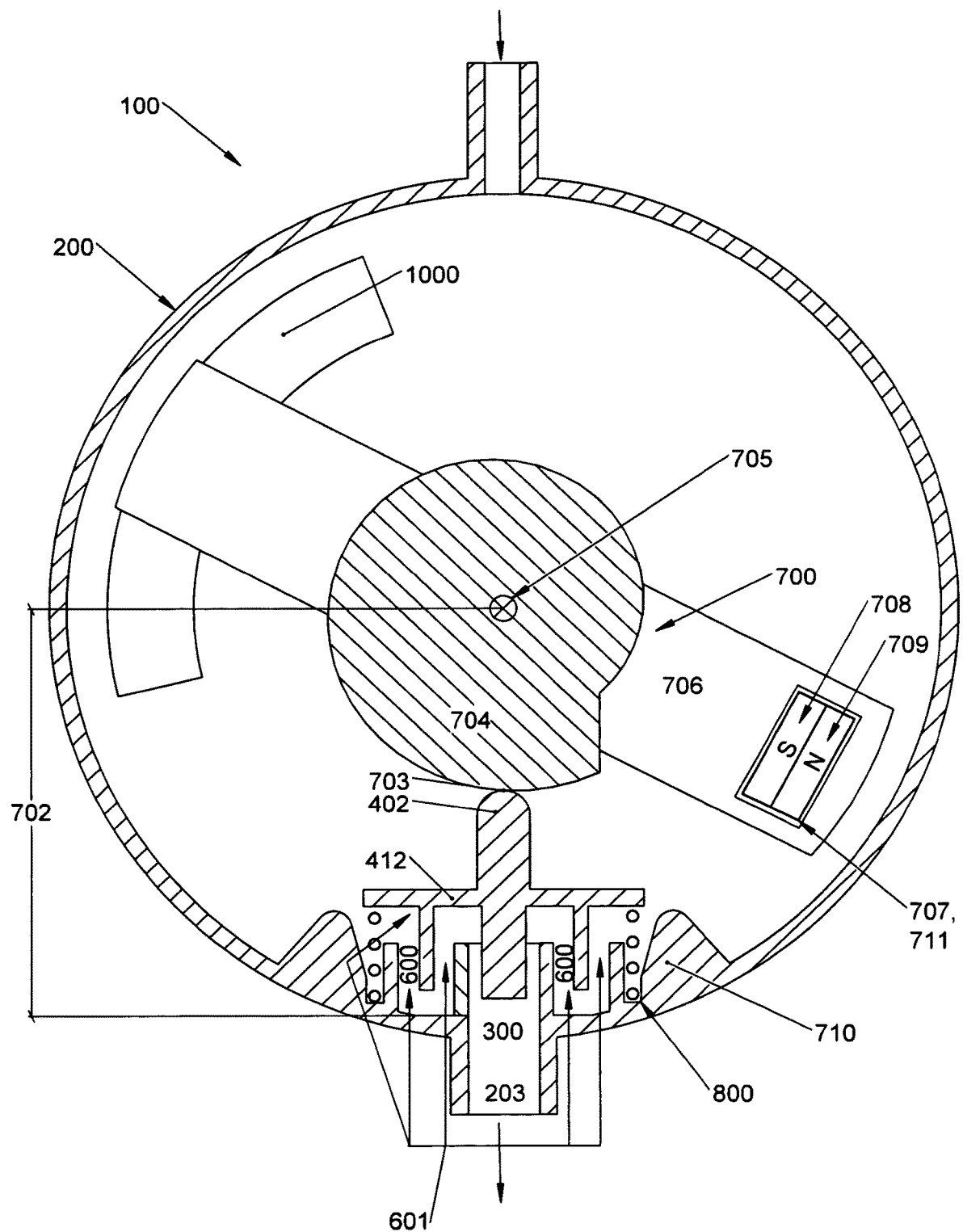
FIG. 8 shows an alternative, fifth embodiment of a hydrocephalus valve with a rotor and a magnetic coupling element.

FIG. 8 shows the hydrocephalus valve 100 illustrated in FIG. 7 with a rotor 706 and with a magnetic coupling member 711 with magnet 707, a north pole 708 and a south pole 709. The adjusting unit 700 comprises multiple parts, including a cam disk 704, a rotor 706 and a pivot arm 1050 or a rotor 706 with pivot arm 1050 or a cam disk 704 with pivot arm 1050. The cam disk 704 is mounted together with the rotor 706 on the axle 705 as one assembly. The rotor 706 comprises a pivot arm 1050 or may be formed as a pivot arm 1050. Furthermore, the cam disk 704 and the rotor 706 are connected to one another. In a preferred embodiment, they are screwed, adhesively bonded or welded together or are formed from one piece. The connection between rotor 706 and cam disk 704 results in the common rotation/pivoting movement thereof, such that a rotation of the rotor 706 or of the pivot arm 1050 or of an additional pivot arm 1050 corresponds to a proportional rotation of the rotor 704. Here, the proportionality follows the offset of the cam disk 704 on the rotor 706. In a further preferred embodiment, two stops 710 are formed into the casing 200 in order to prevent a collision between magnet 707 or rotor 706 and spring 802 or sleeve 412. In the preferred embodiment, the size of the gap 600 between outlet 203 and sleeve 412 may be adjusted by virtue of said sleeve being inserted into the passage 300 or being pushed out of the passage 300 by way of a rotational/pivoting movement of the rotor 706. Here, the sleeve 41 is pushed out of the passage by way of a spring 801, 802. The spring is held in its spring seat 800. This may be described by way of a parameterization of the spacing 702.

In a further embodiment, a brake 1000 is provided in the hydrocephalus valve 100 in order to secure a set rotational angle of the rotor 706. For this purpose, the brake 1000 blocks the freedom of rotation of the rotor 706 or of the pivot arm 1050 thereof. In a preferred embodiment, the brake 1000 blocks the rotor 706 by virtue of frictional engagement being activatable and deactivatable between said brake and a rotor surface. In an alternative embodiment, the brake 1000 imparts a blocking action by virtue of an electromagnetic force field fixing the rotor 706 in a desired position.

In an independent variant, a multiplicity of different valves is combined with one another.

Figure 9:
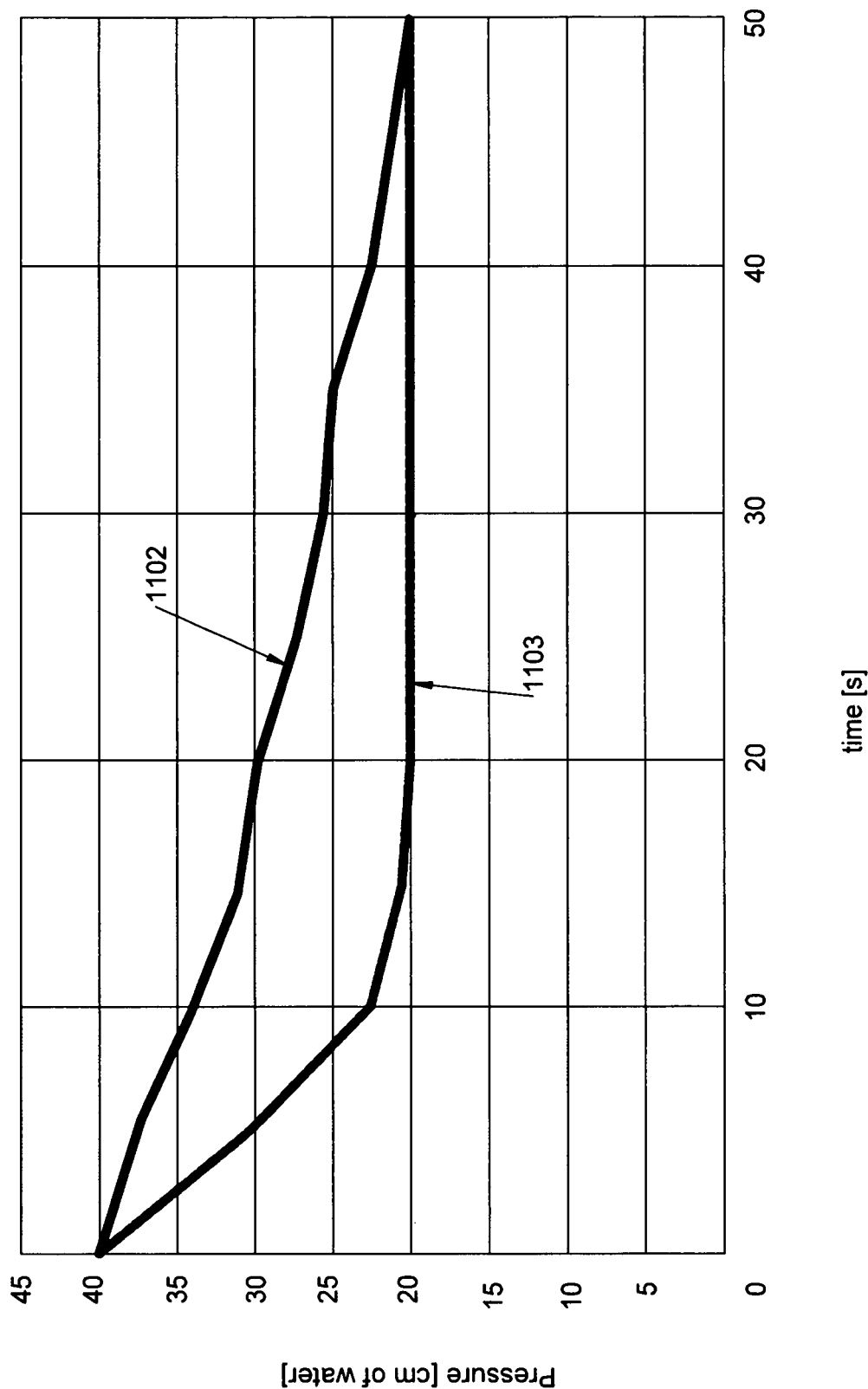
FIG. 9 shows various pressure curves.

FIG. 9 shows, on the basis of a conventional hydrocephalus valve with spring-loaded ball as closing device and with a conventional drainage line, a record of the fluid pressure versus the time. Here, a pressure curve 1103 has been obtained. The pressure curve 1103 shows that a fluid pressure of 40 cm water column has been dissipated within around 10 seconds to a normal level of approximately 20 cm water column. Firstly, with this rate of pressure dissipation, many patients will feel discomfort. Secondly, the pressure curve for different patients with different ventricular system sizes can be obtained only if it can be adjusted by way of structural parameters. If this is the case, it can be set in a patient-specific manner; it can be adjusted to a setpoint profile. Therefore, provision is made for drainage, or the drainage rate thereof, to be made adjustable in order to realize a pressure dissipation which, over a longer time, preferably over at least 20 seconds, even more preferably over at least 30 seconds and most preferably over at least 40 seconds, yields the same effect for the patient irrespective of the patient. The pressure dissipation is preferably distributed over at most 60 seconds, even more preferably over at most 50 seconds.

The pressure curve 1103 in FIG. 9 shows a profile of the pressure curve over 50 seconds. The pressure curve 1103 plotted versus the time (abscissa) in seconds exhibits an inclination relative to the abscissa which is dependent on the scale for the pressure values (ordinate) and to the scale for the seconds (abscissa). The scope of the invention encompasses everything which, in the case of equal scales for pressure values and seconds, has an identical or reduced inclination with respect to the abscissa, assuming the inclination is no lower than in the case of a distribution of the pressure dissipation over 60 seconds, preferably no lower than in the case of a distribution of the pressure dissipation over 50 seconds.

FIG. 10 shows a preferred embodiment of a variant of the hydrocephalus valve as a valve combination 1100.

The adjustable valve combinations discussed below are, in the case of electronic control together with a pressure measurement (not illustrated), capable of implementing a desired pressure curve 1103 (FIG. 9) without further auxiliary measures. They are, in combination, even in combination with conventional hydrocephalus valves, also capable of at least approximately implementing a desired pressure curve 1103 on a purely mechanical basis. The valve combination is schematically illustrated in FIG. 10. According to FIG. 10, said valve combination comprises a drainage line 1102. A conventional hydrocephalus valve and one of the hydrocephalus valves 100 discussed below are installed in the drainage line 1102.

Alternatively, FIG. 10 shows the invention as an interconnection of a conventional valve with a valve combination 1100, that is to say an extended valve combination.

FIG. 11 shows a hydrocephalus valve 100 in a sectional view from above. FIG. 11 shows FIG. 1 on a smaller scale. The hydrocephalus valve 100 includes a liquid-tight casing 200, which is equipped with an inlet 202 and an outlet 203. An axle 705 is arranged in the casing 200. A rotor 706 is seated on the axle. The rotor 706 forms a cam disk 704 with a first cam track 712. A coupling element, a pin 400, slides with its second end 402 on the first cam track 712. The pin 400 is held, so as to be movable in a radial direction with respect to the axle 705, between guides 405 of the casing 200. At the oppositely situated first end 401 of the pin 400, there is provided a body 500 in the form of a plug. The body 500 has a conical tip and a collar 510. As per FIG. 11, the collar 510 can sealingly close against a sealing surface 304 of the casing 200. This prevents an undesired escape of fluid. Here, the plug is pushed outward in a radial direction by the cam track 712. When the rotor 706 is pivoted counterclockwise in FIG. 11, the radius of the cam track 712 decreases. Here, the pin 400 remains in contact with the cam track 712. This is realized under the pressure of a spiral spring 803. The spiral spring 803 is seated with one end in a recess of the conical tip. The spiral spring 803 is supported at the other end on a web 804 of the outlet 203. If the pin 400 is moved in a radial direction into the casing 200 under the pressure of the spiral spring 802, a passage for fluid forms between the plug and the sealing surface on the casing. In the exemplary embodiment in FIG. 1, the cam disk 706 is seated fixedly on the axle, and the axle is connected to an electrical stepper motor (not illustrated). The stepper motor is activated by a storable controller. In the controller, there is stored a profile with respect to time, which is desired in FIG. 9, of the pressure drop in the fluid. In the controller, with the aid of an algorithm, said profile is compared with the pressure values of a pressure measuring device (not illustrated). The difference between the two values leads to a control impulse on the electrical stepper motor.

FIG. 12 illustrates FIG. 5 on a smaller scale. The exemplary embodiment of FIG. 12 differs from the exemplary embodiment of FIG. 11 in that the body 500 is a wedge 506, or is a wedge-shaped plug, which projects into a matching outflow. In the exemplary embodiment, this means that the outflow surrounds the wedge-shaped plug with a spacing in all positions. The spacing arises correspondingly to the dimensions of the plug at the face surface and in a manner dependent on the respective position of the wedge-shaped plug. Wedges 506 have a rectangular cross section with two sides which are inclined relative to one another and two sides which are parallel to one another. The wedge-shaped plug is, like the plug in FIG. 11, held by way of a pin which is not illustrated here. Also, in the embodiment in FIG. 12, a spiral spring 803 is provided which ensures permanent contact of the pin with the cam disk. By contrast to the situation in FIG. 1, the spiral spring 803 is seated not on the tip of the plug but on the pin, wherein a collar 510 is seated on the pin. The spring is situated between the collar and the casing inner wall, wherein the spring surrounds the pin and the plug. The wedge-shaped plug has a different rotational and pivoting drive, specifically a rotor 706, than a conventional hydrocephalus valve, together with a conventional arresting facility between two adjusting processes. As discussed above, the rotor is particularly commonly moved by way of magnets, of which one part is installed in the rotor and the other part is arranged in an adjusting device which is placed over the implanted valve onto the skin of the patient and, by pressing, releases the arresting action and, by rotation, pivots the rotor. The valve thus created is, as per FIG. 10, combined with a conventional hydrocephalus valve, FIG. 10 and FIG. 12 show a drainage line 1101 (FIG. 10) with a hydrocephalus valve 100, which is designed for adjusting a drainage rate and which is connected downstream of a conventional hydrocephalus valve in the drainage line 1101.

FIG. 13 illustrates FIG. 8 on a smaller scale. FIG. 13 shows a situation in which the casing wall has a spacing to the pivot arm 1050. The spacing arises if a pressing action is exerted on the implanted casing from above by way of the adjusting device for adjusting the cam disk. The casing deforms as a result, such that the pivot arm 1050, which was previously in frictionally engaging contact with the casing inner wall, is released for adjustment purposes. A successful release is signaled by a clicking sound, because the upper part of the casing is designed as a click membrane, that is to say a stepped round membrane (not illustrated). It is preferable, for this purpose, for a multiplicity of steps to be formed into the round membrane (not illustrated). The body 500 with collar 510 is designed as a stepped cover.

FIG. 11, FIG. 12 and FIG. 13 likewise show a body 500 which, in all positions, has a spacing to the surrounding inlet or outlet. In the embodiment as per FIG. 12 and FIG. 13, the body is in indirect contact with a cam disk 704. By contrast to FIG. 11, the contact is made by way of a thickened elongation of the body 500. The discussed collar 510 is illustrated at the transition of the body 500 to its elongation. The spring denoted by 802 is arranged between the collar 510 and the casing inner wall. The spring 802 surrounds a body 500, in this case a plug, and in so doing engages into a centering groove. Furthermore, two described magnets are embedded in cam disk 704 (FIG. 12).

Aside from the above-stated combinations with valves from the figures FIG. 1, FIG. 5 and FIG. 8, further advantageous combinations arise with the embodiments of FIG. 4, FIG. 6 and FIG. 7.

A combination (not illustrated) with the embodiment from FIG. 4 results in a body which is in the form of a spherical plug. The diameter of the spherical plug is greater than the opening width of the inlet or outlet, such that the spherical plug can perform both the role of a valve with open-closed function and also an adjustment of the opening width. Here, the spherical plug is held, by way of a rod, displaceably in a guide. Furthermore, the spherical plug is, by way of an articulated rod, held in articulated fashion with a pivotable rotor in the valve casing. In the exemplary embodiment, for the adjustment of the spherical plug, magnets in the rotor and an adjusting device are provided, which adjusting device likewise has magnets and is placed over the implanted valve onto the skin of the patient and is rotated/ pivoted by hand. Instead of the adjusting device, use may also be made of a storable stepper motor. With a stepper motor, the spherical plug can be moved into any desired position.

A combination (not illustrated) with the embodiment from FIG. 6 makes it possible to form a further valve with a body formed as a pot-like plug, wherein the pot-like plug is seated over an outlet which projects into the valve casing. The pot-like plug is also adjusted by way of a cam disk. Here, the pot-like plug is, like the plug in FIG. 6, guided in a manner which is not illustrated in the valve casing and held in contact with the cam disk by way of a spring. Said plug offers the same usage possibilities as the cylindrical plug as per FIG. 3b. Whereas it is the case in FIG. 3b that the remaining gap between the cylindrical plug and the surrounding, tubular inlet or outlet form the limit value for the fluid flow, it is the case in the exemplary embodiment that the remaining gap (limit value) between the tubular outlet or inlet and the inner shell of the surrounding pot-shaped plug is definitive. As in the case of the plug as per FIG. 3b, opening movements of the plug remain without influence even in the case of the exemplary embodiment if they overshoot the limit value for the opening cross section.

A combination (not illustrated) with the embodiment from FIG. 7 shows a valve which also comprises a cylindrical plug. The cylindrical plug includes an adapted tubular outlet. The tubular outlet surrounds the cylindrical plug with a selected spacing. The cylindrical plug has a collar and, in a radial direction with respect to a cam disk, a thickened elongation. The elongation makes contact with the cam disk. At the contact point, the elongation is rounded. The cylindrical plug is, at the elongation, held in a guide of the casing so as to be displaceable in a radial direction. By way of a spiral spring between the collar and the inner wall of the casing, it is ensured that the plug always remains in contact with the cam disk. By pivoting the cam disk, the opening gap between the collar and the outlet is adjusted. In the case of a reduction of the opening gap, the cam disk pushes the collar outward. In the case of an enlargement of the opening gap, the cam disk provides space such that the plug follows the cam track of the cam disk under the pressure of the spiral spring. The pivoting of the cam disk is performed in the exemplary embodiment by way of magnets, wherein the magnets are situated both in the cam disk and in an adjusting device which, for the purposes of adjustment, is placed over the implanted valve onto the skin of the patient and rotated. In the exemplary embodiment, concentrically with respect to the cylindrical plug and the outlet, provision is also made of a ring-shaped web on the collar and a ring-shaped web on the inner wall of the casing. These webs force the fluid to follow a meandering flow profile. The exemplary embodiment differs by a pivot arm on the cam disk. The pivot arm serves for receiving the magnets. Furthermore, different guidance of the plug in the valve casing is provided.

A preferred form of the above-stated body is the form of a needle. FIGS. 2a, 2b, 3a and 3b show different bodies. Aside from FIG. 2b, these are conical plugs for a valve, wherein the plug has a tip which is thicker than the opening of the inlet or outlet for the fluid. The conical plug may also be regarded as a needle. The embodiment as a needle is part of each above-stated embodiment, for example in FIG. 11, FIG. 12 and FIG. 14.

Owing to the form of a needle, the body or the plug closes the inlet or outlet when the needle is pushed far enough into the inlet or outlet. FIG. 3c shows the open position of the valve, and FIG. 3d shows the closed position. The valve belonging to the plug as per FIGS. 3c and 3d otherwise corresponds to the valve as per FIG. 2a. FIG. 2b shows an exactly cylindrical plug instead of a conical or wedge-shaped plug. The cylindrical plug includes a matching tubular inlet or outlet on the valve, which surrounds the plug with a spacing. Irrespective of the extent to which the cylindrical plug is moved into the inlet or outlet, the spacing between the plug and the surrounding inlet or outlet remains unchanged. The cylindrical plug is suitable for a valve that otherwise has the features of the valve belonging to FIG. 2a. The cylindrical plug is however also suitable for a drainage facility with a single valve in the drainage line and a simultaneous, above-described reduction of the pressure drop. Here, the cylindrical plug and the matching tubular inlet or outlet replace the conventional ball and the conventional valve seat for the ball. Furthermore also provided on the cylindrical plug a collar as per FIG. 1. Here, the collar has a closing function. The collar bears with a closing action against the inner wall of the valve casing. The cylindrical plug is subjected to load by a spring, which determines the opening pressure of the valve. The spring is adjustable in a conventional manner such that the opening pressure is also adjustable. The higher the fluid pressure rises, the further the collar moves away from the closing surface of the inner wall of the valve casing. This however also leads to a greater opening width of the valve only up to a limit. The opening width can become no greater than the gap between the plug and the surrounding inlet or outlet. The greater the flow rate of the fluid through the valve caused by the fluid pressure becomes, the greater the flow resistance becomes. This causes a slowing of the increase of the flow rate and of the pressure drop.

FIGS. 14 to 18 show a preferred embodiment of the invention. This embodiment may also be implemented independently.

Figure 14:
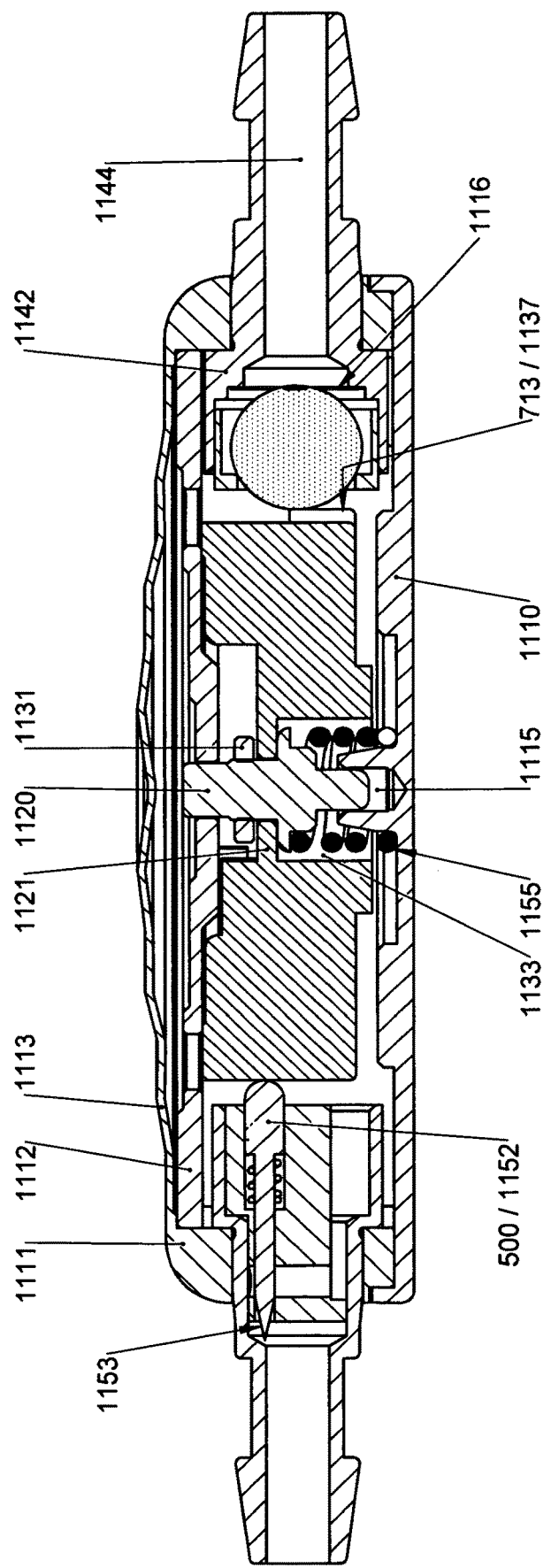
FIG. 14 shows a preferred further embodiment of a hydrocephalus valve in a schematic view from the side in a closed state.

FIG. 14 shows a section through a device 100 with two valves in a common casing, a valve combination 1100. The casing with the two valves is a constituent part a fluid drainage facility or of a shunt of a hydrocephalus patient. The valve combination 1100 is, for this purpose, implanted with corresponding lines (not illustrated), so-called catheters, under the skin of the patient. The lines conduct the fluid from the cranium (not illustrated) of the patient to the device and from there into the abdominal cavity (not illustrated) of the patient, where the body of the patient absorbs the fluid. The casing is composed of a base 1110, a ring 1111 of a ring-shaped support disk 1112 and a cover 1113. An axle 1120 is seated displaceably centrally in the casing. Here, the axle 1120 is held at one end in the support disk 1112 and at the other end in a guide 1114 of the base 1110. The axle 1120 has an outer collar 1121 and is supported with the outer collar 1121 by a spiral spring 1122 on the base 1110.

Also seated on the axle 1120 are a rotor 1130 and a securing ring 1131. Here, the rotor 1130 engages with an inner collar 1132 between the outer collar 1121 and the securing ring 1131. Furthermore, the rotor 1130 surrounds the spiral spring 1122. For this purpose, a corresponding recess 1133 is provided in the rotor 1130. The spiral spring 1122 pushes the rotor 1130 against the support disk 1112 in the casing, such that frictional engagement exists between the rotor 1130 and the support disk 1112, and the rotor 1130 is arrested in the respective position. In this position, the cover 1113 has an outwardly directed bulge. The arresting action can be released by virtue of the casing being subjected to a pressing action by way of an adjusting device which is placed over the casing onto the skin of the patient. Alternatively, the brake may also be released by manually pressing on the cover 1113.

The pressure leads to an indentation of the cover 1113 and to a displacement of the axle 1120 toward the base 1110. Here, the axle 1120 can be displaced in the cavity 1115 of the guide 1114. Even a small displacement of the axle 1120 leads to a release of the rotor 1130 from the support disk 1112. The rotor 1130 can subsequently be pivoted. For the pivoting of the rotor 1130, magnets 1134 are installed in the rotor 1130 at diametrically oppositely situated positions.

FIG. 14 shows a situation of an invention 100, 1100 with a ball 1141 in the case of a deactivated valve. Here, the ball 1141 is pushed by a plate spring 1147 a valve seat. FIG. 14 shows a second insert 1151. Arranged displaceably in the insert 1151 is a body 500, 1152 in the form of a cylindrical closing part 1152, for example in the form of a needle 1152. The needle 1152 projects with a conical tip 1153 into the gap passage 1154, a small channel, a gap. The position of the tip 1153 determines the opening width of the gap passage 1154 for the passage of fluid. The greater the distance by which the tip 1153 extends into the gap passage 1154, the smaller the opening width for the passage of fluid into the outlet 1150 becomes. The smaller the distance by which the tip 1153 extends into the gap passage 1154, the larger the opening width for the passage of fluid becomes.

Figure 15:
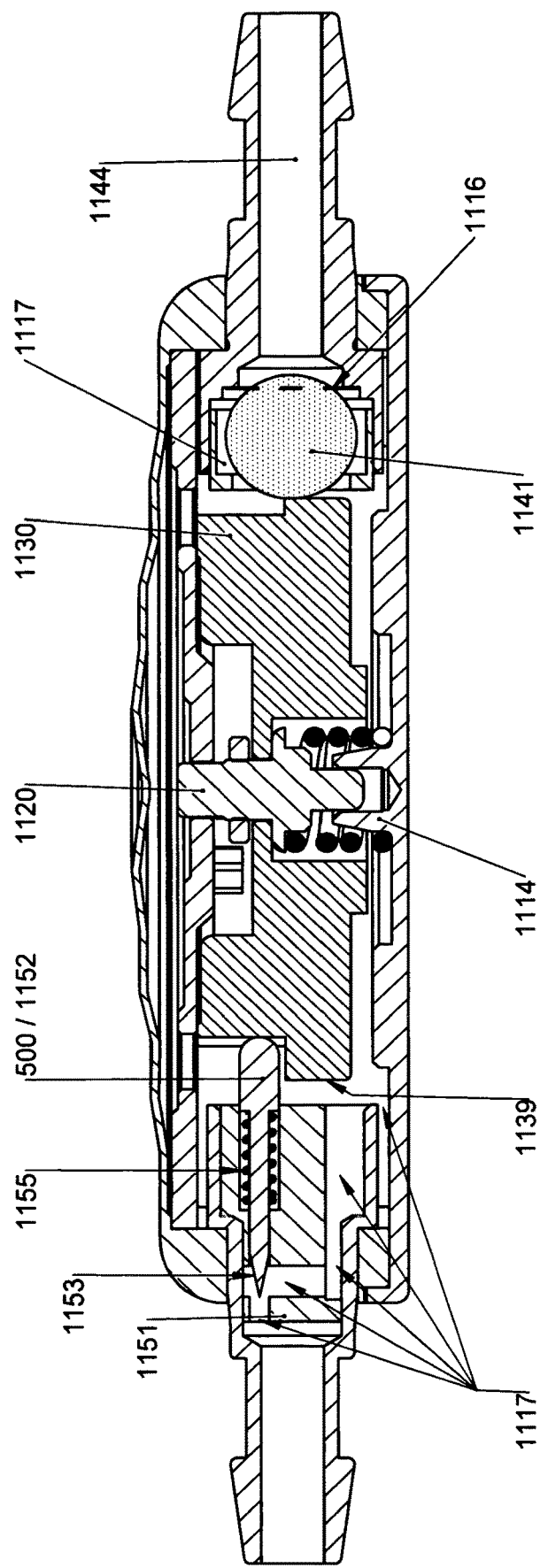
FIG. 15 shows a further embodiment of a hydrocephalus valve in a schematic view from the side in an opened state.

The position of the tip 1153 or of the closing part 1152 is likewise determined by a second cam track 714 on the rotor 1130. In FIGS. 14 and 15, the cam track 714 for the closing part 1152, a body 500, that is to say the needle 1152, runs above the first cam track 712 for the ball 1141 for the differential pressure valve 1140b or a gravitational valve 1140a (not illustrated). The second cam track surface 715 is formed by the contact surface of the needle 1152 with the rotor 1130. The first cam track surface 713 is formed by the contact surface of the ball 1141 and the first cam track 712. The rotor 1130 is mounted on an axle 1120. An outer collar 1121 of the axle 1120 supports the inner collar 1132 of the rotor 1130 and is held by a securing ring 1131. For this purpose, the axle 1120 is seated in a recess 1133 of the rotor 1130.

As in the case of the ball 1141, permanent contact of the closing part 1152, the needle 1152, with the rotor 1130 is provided, such that the needle 1152 permanently follows the cam track 715 provided for it. For this purpose, the needle 1152 is surrounded by a spiral spring 1155, which pushes the needle 1152 against the rotor. The spiral spring 1155 is, for this purpose, supported with one end in the insert 1151. With the other end, the spiral spring presses against the needle 1152.

FIG. 15 shows the invention as per FIG. 14 in the same sectional illustration but different pivoting position of the rotor 1130, in an opened state. The spiral spring 1155 pushes the needle 500, 152 out of the gap passage 1154, such that the channels 1117 can be flowed through by fluid. Furthermore, matching magnets 1134 are situated in the adjusting device, such that a rotation of the adjusting device about the axle 1120 in its guide 1114 by way of the attraction force of the magnets 1134 causes a pivoting of the rotor. If, after a desired pivoting movement, the adjusting device is removed again, a renewed automatic arresting of the rotor occurs. By pivoting of the rotor 1130, a gravitational valve 1140a (not illustrated) or a differential pressure valve 1140b in the casing can be activated or deactivated.

The gravitational valve 1140 or the differential pressure valve 1140b is arranged at the inlet side in the casing. The flow direction is denoted by 1146. The gravitational valve 1140a or the differential pressure valve 1140b includes a ball 1141 The ball 1141 is seated in an insert 1142 in its valve seat 1116. The insert 1142 projects with a connection grommet 1143 through an opening in the ring 1111 of the casing. The connection grommet 1143 serves for the connection of a hose line.

FIG. 15 shows the differential pressure valve 1140b open in a recumbent position of the patient. The rotor 1130 pushes with a first contact surface, first cam track surface 713, against the outer wall of the ball, such that the latter is moved in the direction of the opening 1144 counter to the spring force of a plate spring 1147 in the first insert 1142. As a result of this movement, channels 1117 are opened up, such that inflowing fluid can pass. Because channels 1117 lead through the casing, the fluid can flow through the invention.

For the case that a gravitational valve 1140a is installed and the patient with the valve position illustrated in FIG. 15 assumes a standing position, the gravitational valve 1140a closes under the pressure of the ball 1141. Independently of this, the gravitational valve 1140 can be deactivated, such that a fluid flow is always prevented, even in the recumbent position of the patient.

In order to move from the cam track surface illustrated in FIG. 14—closed—to the cam track surface illustrated in FIG. 15—open—, the rotor 1130 must be pivoted to a certain extent. This is performed in the manner described above by way of the adjusting device. Channels 1117 are also situated in another insert 1151, which is arranged at the outlet side.

FIGS. 14 and 15 show different positions of the closing part 1152. In FIG. 14, the tip 1153 has moved a great distance into the gap passage 1154. In FIG. 14, the second cam track 714 for the closing part 1152 with the rotor 1130 runs, at the contact surface, with a spacing to the axle 1120 which is large enough for the position of the tip 1153. In FIG. 15, the spacing of the contact surface to the axle 1120 is significantly smaller, such that the tip 1153 is set back in relation to the position in FIG. 14 to this extent, resulting in a greater opening width between the tip 1153 and the gap passage 1154. FIG. 15 therefore shows the invention in an opening state.

Figure 16:
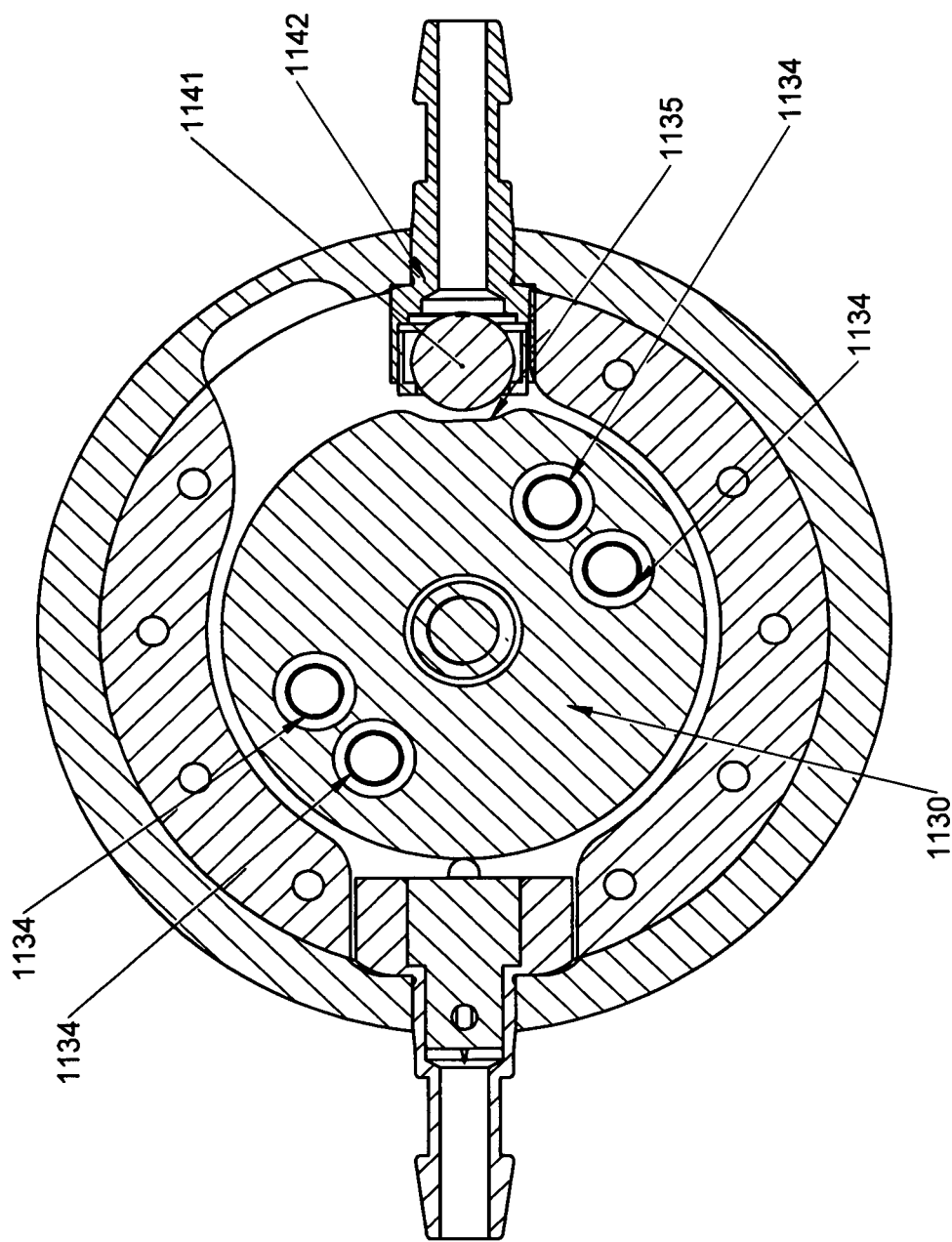
FIG. 16 shows a preferred embodiment in a sectional view.

FIG. 16 shows a section through the device, wherein the central axes of the inserts 1142 and 1151 lie in the section plane. The closing part 1152, the needle 1152, can be seen to a limited extent in the sectional illustration because it has a spacing to the section plane. The ball 1141 is illustrated in the closed position.

The rotor 1130 has an indentation 1135 and a protuberance 1136. In the region of the indentation 1136, the ball 1141 is situated in the closed position. The gravitational valve 1140a or differential pressure valve 1140b is deactivated. In the region of the protuberance 1135, the gravitational valve is opened up again. In the case of stepped opening-up, indentations of smaller depth and/or protuberances of lesser magnitude are also provided between the indentation 1135 and the protuberance 1136. FIG. 16 shows, in the exemplary embodiment, four magnets 1130 for the rotor 1134 the adjustment thereof.

Figure 17:
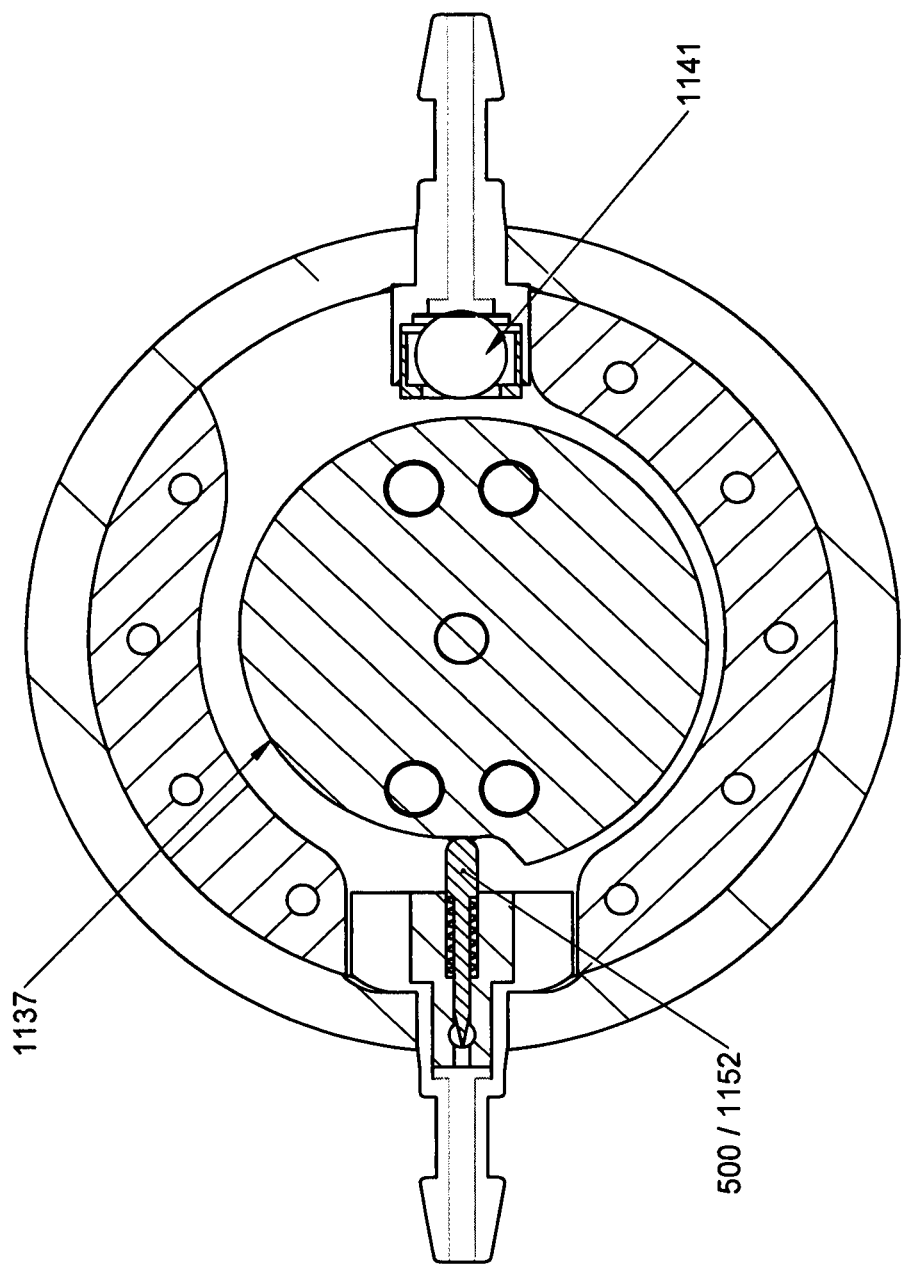
FIG. 17 shows a preferred embodiment in a sectional view.

FIG. 17 shows a section through the device, wherein the central axis of the closing part 1152 lies in the section plane. Here, the section plane runs through the second cam track 714 belonging to the closing part 1152. It can be seen that the second cam track 714 belonging to the closing part 1152 runs in spiral-shaped fashion, such that a continuously variable adjustment of the closing part 1152 between two extreme values is possible.

Preferably, of two valves arranged in one casing, one valve is arranged at the inlet 202 of the casing and the other valve is arranged at the outlet 203 of the casing.

Consideration may also be given to other combinations of valves in a casing. These include combinations of gravitational valves with valves other than differential pressure valves, and also of differential pressure valves with valves other than gravitational valves. The valves other than differential pressure valves also include cam-track-controlled valves. Here, a cam track is guided along on a closing part. The cam track determines the opening and closing positions of the closing part. The guidance of the closing part may be realized in positively locking and/or non-positively locking fashion. Positively locking within the meaning of the invention, and at the same time non-positively locking, is a groove in a rotor, into which groove the closing part engages by way of a journal or the like. The positively locking and non-positively locking connection may also be formed by a rail as cam track, which rail is encompassed by the closing part. It is preferable for only a non-positively locking connection to be provided between the cam track and the closing part. The non-positively locking connection is formed here by a spring, by way of which the closing part is pushed or pulled against the cam track. Even more preferably, the closing part is formed at least partially as a profiled bar and held displaceably in a guide or is connected to a profiled bar which is held displaceably in a guide. Most preferably, a cylindrical profiled bar is provided, which pushes with one end against the cam track under the spring pressure and which corresponds, by way of the other end, with a valve seat. The valve seat may be a ring or a bore in the casing. The bore may widen toward the closing part. The widening may be conical or have some other lateral surface.

It is advantageous if the body, that is to say a needle 1152, is arranged in the second insert 1151, such that the second insert 1151 can be installed together with the needle 1152 in the casing. In the part that protrudes out of the casing, the second insert 1151 forms a connection for a drainage line. At the other end, the insert projects into the casing interior. There, the second insert 1151 forms the guide for the cylindrical closing part, the needle 1151.

At the same time, the second insert 1151 may form a cavity in which the spiral spring 1155 surrounds the cylindrical closing part 1152. For conducting fluid, a bore 1156 may be formed, transversely with respect to the longitudinal axis, in the region of the above-described tip of the second insert, such that the fluid can flow in or flow out past the tip transversely with respect to the longitudinal direction of the insert. At the other end, which is averted from the into the casing bore, the cylindrical closing part 1152 slides on a second cam track 714. Here, the closing part 1152 is pushed by a surrounding spiral spring 1155 against the second cam track 714, such that the closing part 1152 follows any change in the second cam track 714. For the sliding bore of the closing part 1152 on the second cam track, a rounding of the closing part in the region of contact is advantageous. The second cam track 714 may be situated on the face surface and/or on the shell of a rotor 1130. Use is preferably made of a disk-shaped rotor 1130, the circumferential surface of which is designed as second cam track 714 such that the closing part 1152 performs all desired closing movements and opening movements. This is referred to as cam disk 704.

The rotor/cam disk is mounted, pivotably in the valve casing, on an axle. The rotor/cam disk is preferably adjusted by way of magnets. For this purpose, magnets are firstly installed in the rotor/cam disk, and, secondly, an adjusting device with other magnets is provided. The adjusting device is placed onto the skin of the patient over the casing and is rotated. During a rotation of the adjusting device, the rotor/cam disk follows the magnetic force or adjusting force of the adjusting device. After every adjustment, the rotor/cam disk is arrested in the attained position until the next adjustment. The arresting action is realized optionally by clamping of the rotor/cam disk. The clamping may be performed at the circumference or at the face surface of the rotor/cam disk. For the clamping at the circumference, the casing may be utilized by virtue of a casing being used which has a flexible cover and flexible side walls, such that, when a pressure is exerted on the casing cover, the side walls bulge outward and release the rotor. When the pressure is released, the casing springs back and encloses the rotor/cam disk between the side walls.

The pressure required for the casing deformation is generated by way of the adjusting device. The adjusting device is therefore firstly pressed against the casing cover, in order to eliminate the arresting action, before the pivoting is performed.

For the clamping of the rotor at the face surface, an axle which is adjustable in an axial direction is preferably provided in the casing. The axle is subjected to the pressure of a spring, which pushes the rotor in frictionally engaging fashion against a slightly outwardly bulged cover. As soon as the axle is displaced to a certain extent in an axial direction owing to pressure on the cover, the rotor releases from the cover. The certain extent is a slight inward indentation of the cover. The rotor can subsequently be rotated in the above-described manner. The pressure is generated by way of the adjusting device as in the case of an arresting action at the circumference; the same applies for the rotation. The displacement is possible in the casing because a corresponding clearance is provided between the end of the axle and the base of the casing. The axle has a collar by way of which it engages behind the rotor formed as cam disk. The spring by way of which the arresting pressure is exerted on the rotor/cam disk by the axle and the collar thereof is arranged between the casing base and the collar of the axle. Additionally, on that side of the rotor which faces toward the cover, there may be mounted a ring which forces the rotor to lift off from the cover in the event of an inwardly directed deformation of the cover. The ring is, for this purpose, fastened to the rotor or to the axle.

The differential pressure valve described above may be combined with other valves. Here, the differential pressure valve may be arranged upstream or downstream of the other valve in a flow direction/drainage direction. In combination with another valve, the closing body of which is spring-loaded and which opens in accordance with the fluid pressure, the above-described valve may be utilized to dampen the drainage rate, that is to say to homogenize the pressure drop over a certain period of time.

Gravitational valves are preferably used as other valves.

These gravitational valves may be above-described conventional valves.

The gravitational valve opens to a maximum extent in the recumbent position.

This also leads to a maximum pressure drop.

With the differential pressure valve, the pressure drop can advantageously be homogenized, that is to say made adjustable in a patient-specific manner.

A special gravitational valve, specifically a switchable gravitational valve, is optionally inserted in the casing. The gravitational valve can be activated and deactivated. For this purpose, an actuating device/switching device is preferably provided in operative connection with the closing part of the gravitational valve.

The length of the indentations on the rotor/cam disk on the circumference or on the face surface of the rotor/cam disk is determined, in the case of a combination of the gravitational valve with a second, adjustable valve, from the adjustment range desired for the second valve.

The above-described gravitational valve may also, independently of the combination with a second valve, have advantages for the fluid drainage. That is to say, the described gravitational valve may also be advantageous as sole valve for the control of the fluid flow.

As soon as the form of the individual cam tracks and the rotational position or pivoting position of the associated rotor/cam disks are defined, it may also be advantageous to provide a common rotor/cam disk for both valves in the common casing. Then, on the common rotor/cam disk, two cam tracks are provided, one of which is designed for one valve and the other of which is designed for the other valve. The two cam tracks than preferably lie in different, mutually parallel planes. It is however also possible for both cam tracks to lie in a common plane. The cam tracks then preferably extend on different circumferential surfaces.

After a pivoting/rotation of the rotor/cam disks, arresting of the rotor/cam disk is performed, such that an undesired adjustment is prevented. The arresting action is released prior to the adjustment and reactivates after every adjustment. Such an adjustment may be realized with different embodiments. In one embodiment, a toothing is provided on the casing and on the rotor. If the toothings engage into one another, the rotor/cam disk is blocked. The blocking is released by virtue of the toothings being moved apart.

Other embodiments are based on the casing bearing in frictionally engaging fashion against the rotor/cam disk in the arresting position. To release the arresting action, the casing is deformed so as to lift off from the rotor/cam disk. The deformation required to release the arresting action is preferably performed by way of the adjusting device for rotating the rotor. To release the arresting action, the adjusting device is not only placed over the implanted valve onto the skin of the patient, but is also pressed against the valve until the arresting action has been released by deformation of the casing. After the lift-off of the adjusting device, the casing automatically springs back and engages the arresting action.

FIG. 18 shows a preferred embodiment of a rotor in a plan view. It is possible to see two different stages, each outer edge of which is a cam track. The lower stage is characterized by a first cam track 712, and the upper stage is characterized by a second cam track 714. An indentation 1135 has been formed into the lower stage; a protuberance 1136 can be seen.

LIST OF REFERENCE DESIGNATIONS

100 Hydrocephalus valve
200 Casing
201 Casing interior
202 Inlet
203 Outlet
204 Pipe
205 Pipe outer diameter
300 Passage
301 Passage end
302 Passage direction
303 Cross-sectional area
304 Passage inner surface
306 Funnel-shaped inlet
307 Hose-like portion
308 Outlet bushing
400 Coupling element
401 First end 402 Second end
403 Mechanism member
404 Journal
405 Linear bearing
406 Plug
407 Closure end
408 Contact portion
409 Neck portion
410 Collar portion
411 Elongation portion
412 Sleeve
413 Sleeve inner diameter
414 Sleeve length
415 Pipe end
416 Central plug
417 Edge
500 Body
501 -
502 Body axis
503 Body lateral surface
504 First body end
505 Second body end
506 Wedge
507 Wedge face surface
508 Transition edge
509 Rod
510 Collar
600 Gap
601 Passage volume
602 Gap length
700 Adjusting unit
701 Direction
702 Spacing
703 Contact point
704 Cam disk
705 Axle
706 Rotor
707 Magnet
708 North pole
709 South pole
710 Stop
711 Magnetic coupling member
712 First cam track
713 First cam track surface
714 Second cam track
715 Second cam track surface
800 Spring seat
801 Spring element
802 Spring
803 Spiral spring
804 Web
900 Fluid
1000 Brake
1050 Pivot arm
1100 Valve combination
1101 Second valve
1102 Drainage line
1103 Pressure curve
1110 Base
1111 Ring
1112 Support disk
1113 Cover
1114 Guide
1115 Cavity
1116 Valve seat
1117 Channel
1120 Axle
1121 Outer collar
1122 Spiral spring
1130 Rotor
1131 Securing ring
1132 Inner collar
1133 Recess
1134 Magnets
1135 Indentation
1136 Protuberance
1140a Gravitational valve
1140b Differential pressure valve
1141 Ball
1142 First insert
1143 Connection grommet
1144 Opening
1145 Valve seat
1146 Flow direction
1147 Plate spring
1150 Outlet
1151 Second insert
1152 Body (needle)
1153 Tip
1154 Gap passage
1155 Spiral spring
1156 Bore

The invention claimed is:
1. A hydrocephalus valve for draining fluid from a ventricular system of a patient, comprising:
  a casing (200) having a casing interior (201);
  a passage (300) extending in a passage direction (302) for draining fluid,
  a body (500, 506, 1152) which is arranged in the casing interior (201), wherein the body (500, 506, 1152) is movable in the passage direction;
  an adjusting unit (700, 704, 706); and
  an adjustable gap (600) arranged around the body within the passage,
  wherein the adjusting unit (700, 704, 706) is configured to move the body along the passage direction (302) into a defined position,
    in which the adjustable gap is permanently open, and thereby adjust a drainage rate in the passage between 1 ml per hour and 1000 ml per hour in order to slow or accelerate a change in pressure in the ventricular system resulting from the drainage, and
  wherein the body remains in the defined position independently of the pressure in the ventricular system.
2. The hydrocephalus valve as claimed in claim 1,
  wherein the body (500, 506) is a guided plug, wedge, cone, profiled rod or a ball.
3. The hydrocephalus valve as claimed in claim 1,
  wherein the body (500, 506, 1152) has a collar (510),
  wherein, between the collar (510) and at least one surface portion of the adjusting unit, there is provided a spring (802, 1155) which ensures permanent contact of the body (500, 506, 1152) with the surface portion.
4. The hydrocephalus valve as claimed in claim 1,
  wherein the passage (300) is at least one first valve inlet (202).
5. The hydrocephalus valve as claimed in claim 1,
  wherein the passage (300) is an outlet (203).
6. The hydrocephalus valve as claimed in claim 5,
  wherein the body is a profiled rod (1152),
  wherein the profiled rod (1152) projects with a tip (1153) into an opening (1144) of the outlet.

7. The hydrocephalus valve as claimed in claim 1, wherein the adjusting unit (700) comprises a cam disk (704).

8. The hydrocephalus valve as claimed in claim 7, wherein the cam disk (704) has an axis (705), and wherein the axis (705) is arranged in front of the passage (300).

9. The hydrocephalus valve as claimed in claim 1, wherein the adjusting unit (700) comprises at least one rotor (706).

10. The hydrocephalus valve as claimed in claim 9, wherein the adjusting unit comprises at least one magnet (707, 1134).

11. The hydrocephalus valves as claimed in claim 10, wherein the rotor (706) is formed so as to be connected to the magnet (707, 1134) and the rotor (706) is formed so as to be connected to the adjusting unit (700).

12. The hydrocephalus valve as claimed in claim 1, wherein a movement of the adjusting unit (700) is a partial rotation and/or one rotation and/or a number of rotations or a sliding movement or a stroke movement.

13. The hydrocephalus valve as claimed in claim 1, wherein the adjusting unit (700) controls a movement of the body (500, 506, 1152) along a cam track.

14. The hydrocephalus valve as claimed in claim 13, wherein the cam track (712, 714) is formed by a circumferential surface or a face surface of the adjusting unit (700, 704) or of a rotor (706).

15. The hydrocephalus valve as claimed in claim 13, wherein the body (500, 506, 1152) bears under spring pressure against the cam track.

16. The hydrocephalus valve as claimed in claim 13, wherein a first end of the body (500, 506, 1152) bears against the cam track.

17. The hydrocephalus valve as claimed in claim 13, wherein a first end with a rounded portion of the body (500, 506, 1152) bears against the cam track.

18. The hydrocephalus valve as claimed in claim 1, wherein the passage (300) is at least one first valve outlet (203), and wherein the outlet (203) has a tubular form with a cylindrical inner shell.

19. The hydrocephalus valve as claimed in claim 1, wherein the passage (300) is at least one first valve outlet (203), and wherein the outlet (203) is formed by an insert (1152) of the casing, and a guide for the body (500, 506, 1152) is formed by the insert of the casing.

20. The hydrocephalus valve as claimed in claim 19, wherein a first end of the body (500, 506, 1152) is supported in the insert (1151).

21. An arrangement, comprising:
at least one hydrocephalus valve as in claim 1; and
at least one second valve arranged upstream or downstream of the hydrocephalus valve in a flow direction of the fluid.

22. The arrangement as claimed in claim 21, wherein the hydrocephalus valve and the second valve are arranged in a flow path.

23. The arrangement as claimed in claim 21, wherein the second valve is a differential pressure valve (1140b).

24. The arrangement as claimed in claim 21, wherein the second valve has a spring-loaded closing part which closes and opens in a manner dependent on the fluid pressure.

25. The arrangement as claimed in claim 21, wherein a common casing is provided for both valves.

26. The arrangement as claimed in claim 25, wherein the casing comprises an inlet and an outlet, wherein,
the hydrocephalus valve is arranged on the inlet and the second valve is arranged on the outlet, or
the second valve is arranged on the inlet and the hydrocephalus valve is arranged on the outlet, and
wherein channels are provided in the casing from the hydrocephalus valve to the second valve, which channels have a lower flow resistance than a connection of the two valves to a drainage line as are provided for the feed of fluid to the common casing and/or for the drainage of fluid from the common casing.

27. A hydrocephalus valve for draining fluid from a ventricular system of a patient, comprising:
a casing (200) having a casing interior (201);
a gravitational valve (1140a) or a differential pressure valve (1140b) arranged at an inlet in the casing (200);
an outlet passage (300) extending in a passage direction (302) for draining fluid,
a body (500, 506, 1152) which is arranged in the casing interior (201), wherein the body (500, 506, 1152) is movable in the passage direction;
an adjusting unit (700, 704, 706); and
an adjustable gap (600) arranged around the body within the outlet passage,
wherein the adjusting unit (700, 704, 706) is configured to move the body along the passage direction (302) and, when the hydrocephalus valve is implanted in a patient, thereby adjust a drainage rate in the passage between 1 ml per hour and 1000 ml per hour in order to slow or accelerate a change in pressure in the ventricular system resulting from the drainage.

28. A hydrocephalus valve for draining fluid from a ventricular system of a patient, comprising:
a casing (200) having a casing interior (201);
a passage (300) extending in a passage direction (302) for draining fluid,
a body (500, 506, 1152) which is arranged in the casing interior (201), wherein the body (500, 506, 1152) is movable in the passage direction;
an adjusting unit (700, 704, 706);
a spring arranged to push the body towards the adjusting unit (700, 704, 706); and
an adjustable gap (600) arranged around the body within the passage,
wherein the adjusting unit (700, 704, 706) is configured to push the body against a force of the spring along the passage direction (302) and thereby adjust a drainage rate in the passage between 1 ml per hour and 1000 ml per hour in order to slow or accelerate a change in pressure in the ventricular system resulting from the drainage.

* * * * *